(12) United States Patent
Lusted

(10) Patent No.: US 10,709,339 B1
(45) Date of Patent: Jul. 14, 2020

(54) BIOMETRIC WEARABLE FOR CONTINUOUS HEART RATE AND BLOOD PRESSURE MONITORING

(71) Applicant: Senstream, Inc., San Francico, CA (US)

(72) Inventor: Hugh Lusted, Oregon House, CA (US)

(73) Assignee: Senstream, Inc., San Francisco, CA (US)

( * ) Notice: Subject to any disclaimer, the term of this patent is extended or adjusted under 35 U.S.C. 154(b) by 0 days.

(21) Appl. No.: 16/026,450

(22) Filed: Jul. 3, 2018

Related U.S. Application Data

(60) Provisional application No. 62/528,336, filed on Jul. 3, 2017.

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/0006* (2013.01); *A61B 5/0022* (2013.01);
(Continued)

(58) Field of Classification Search
CPC combination set(s) only.
See application file for complete search history.

(56) References Cited

U.S. PATENT DOCUMENTS 5,964,701 A * 10/1999 Asada ................ A61B 5/02438
600/300
6,402,690 B1 * 6/2002 Rhee .................... A61B 5/0002
600/300
(Continued)

OTHER PUBLICATIONS

Goli, Surenda et al., "Cuffless Continuous Non-Invasive Blood Pressure Measurement Using Pulse Transit Time Measurement", International Journal of Recent Development in Engineering and Technology, online at www.irjrdet.com, vol. 2, Issue 1, Jan. 2014, pp. 86-91.

(Continued)

*Primary Examiner* — Michael W Kahelin
*Assistant Examiner* — Shirley X Jian
(74) *Attorney, Agent, or Firm* — O'Banion & Ritchey LLP; John P. O'Banion

(57) ABSTRACT

A wearable biometric sensing ring apparatus for continuous heart rate and blood pressure monitoring having a ring housing for retention on a finger of a user, a photoplethysmograph (PPG) sensor disposed within the housing on an interior surface of the ring to contact or be placed adjacent the finger to register a pulse rate of the user, a first electrode and second electrode disposed within the housing on said interior surface of the ring to contact the finger on a first side of the user's body, and a third electrode disposed on an exterior surface of the ring housing to contact a contralateral portion of the user's body. A combination of first, second and third electrodes are configured for obtaining electrocardiogram (ECG) measurements. A controller and programming are provided for receiving analog pulse rate data from the PPG sensor and analog ECG data from the first, second and third electrodes, converting the analog pulse rate data and ECG data into digital data, calculating one or more of heart rate (HR), heart rate variability (HRV) and blood pressure (BP) from a combination of the digital ECG and PPG sensor data, and graphically outputting one or more of the calculated HR, HRV and BP.

20 Claims, 26 Drawing Sheets

(51) Int. Cl.
  *A61B 5/0408* (2006.01)
  *A61B 5/0245* (2006.01)
  *A61B 5/024* (2006.01)
  *A61B 5/021* (2006.01)
  *A61B 5/053* (2006.01)

(52) U.S. Cl.
  CPC ........ *A61B 5/04085* (2013.01); *A61B 5/4035* (2013.01); *A61B 5/6826* (2013.01); *A61B 5/7425* (2013.01); *A61B 5/0245* (2013.01); *A61B 5/02125* (2013.01); *A61B 5/02405* (2013.01); *A61B 5/02427* (2013.01); *A61B 5/02438* (2013.01); *A61B 5/0531* (2013.01); *A61B 2560/0214* (2013.01); *A61B 2560/0468* (2013.01); *A61B 2562/0209* (2013.01); *A61B 2562/043* (2013.01)

(56) References Cited

U.S. PATENT DOCUMENTS

| | | | |
|---|---|---|---|
| 6,413,223 B1* | 7/2002 | Yang | A61B 5/021 600/485 |
| 6,527,711 B1* | 3/2003 | Stivoric | A61B 5/0002 128/898 |
| 6,605,038 B1* | 8/2003 | Teller | A61B 5/411 600/300 |
| 6,608,562 B1* | 8/2003 | Kimura | A61B 5/02427 128/903 |
| 7,020,508 B2* | 3/2006 | Stivoric | A61B 5/0205 |
| 7,261,690 B2* | 8/2007 | Teller | A61B 5/02055 |
| 7,285,090 B2* | 10/2007 | Stivoric | A61B 5/01 600/300 |
| 7,547,279 B2* | 6/2009 | Kim | A61B 5/02405 128/920 |
| 8,568,330 B2* | 10/2013 | Mollicone | A61B 5/024 600/508 |
| 8,602,997 B2* | 12/2013 | Banet | A61B 5/02125 600/485 |
| 9,237,869 B1* | 1/2016 | Lee | A61B 5/6804 |
| 9,311,825 B2 | 4/2016 | Lusted | |
| 9,522,317 B2* | 12/2016 | Bleich | A63B 69/0028 |
| 9,582,035 B2* | 2/2017 | Connor | G06F 1/163 |
| 9,707,466 B2* | 7/2017 | Bleich | A63B 69/0028 |
| 9,711,060 B1 | 7/2017 | Lusted | |
| 9,993,176 B2* | 6/2018 | Kwon | A61B 5/6802 |
| 10,076,252 B2* | 9/2018 | Saponas | A61B 5/02233 |
| 10,092,203 B2* | 10/2018 | Mirov | A61B 5/04085 |
| 2002/0026114 A1* | 2/2002 | Nissila | A61B 5/02438 600/384 |
| 2003/0023145 A1* | 1/2003 | Lee | A61B 5/02055 600/300 |
| 2004/0015094 A1* | 1/2004 | Manabe | A61B 5/0492 600/546 |
| 2005/0231686 A1* | 10/2005 | Rathjen | A61B 3/16 351/205 |
| 2007/0299322 A1* | 12/2007 | Miyajima | A61B 5/0008 600/301 |
| 2008/0058622 A1* | 3/2008 | Baker | A61B 5/14552 600/344 |
| 2008/0081963 A1* | 4/2008 | Naghavi | A61B 5/01 600/301 |
| 2008/0171918 A1* | 7/2008 | Teller | A61B 5/411 600/301 |
| 2008/0208016 A1* | 8/2008 | Hughes | A61B 5/0533 600/301 |
| 2009/0318779 A1* | 12/2009 | Tran | A61B 5/0022 600/301 |
| 2010/0081900 A1* | 4/2010 | Price | A61B 5/14552 600/324 |
| 2010/0160798 A1* | 6/2010 | Banet | A61B 5/02125 600/490 |
| 2010/0168531 A1* | 7/2010 | Shaltis | A61B 5/02241 600/301 |
| 2010/0210924 A1* | 8/2010 | Parthasarathy | A61B 5/0002 600/301 |
| 2010/0324388 A1* | 12/2010 | Moon | A61B 5/746 600/324 |
| 2011/0213197 A1 | 9/2011 | Robertson | |
| 2012/0130203 A1* | 5/2012 | Stergiou | A61B 5/0002 600/301 |
| 2012/0218184 A1* | 8/2012 | Wissmar | G06F 3/0346 345/158 |
| 2013/0095459 A1* | 4/2013 | Tran | A61B 5/6816 434/247 |
| 2013/0116514 A1* | 5/2013 | Kroner | A61B 5/01 600/301 |
| 2013/0183646 A1* | 7/2013 | Lusted | G09B 19/00 434/236 |
| 2013/0226015 A1* | 8/2013 | Lam | A61B 5/02241 600/499 |
| 2014/0215684 A1* | 8/2014 | Hardy | A41D 19/0031 2/160 |
| 2015/0080746 A1* | 3/2015 | Bleich | A63B 69/0028 600/479 |
| 2015/0133193 A1* | 5/2015 | Stotler | G06F 1/163 455/557 |
| 2015/0220109 A1* | 8/2015 | von Badinski | G01P 15/00 340/539.12 |
| 2015/0309535 A1* | 10/2015 | Connor | G06F 1/163 361/679.03 |
| 2015/0327809 A1* | 11/2015 | Tateda | A61B 5/1172 600/324 |
| 2015/0370320 A1* | 12/2015 | Connor | A61B 5/6831 345/173 |
| 2016/0012749 A1* | 1/2016 | Connor | G09B 5/00 600/13 |
| 2016/0128586 A1* | 5/2016 | Parton | A61B 5/02405 600/479 |
| 2016/0192716 A1* | 7/2016 | Lee | G06F 3/015 2/422 |
| 2016/0192856 A1* | 7/2016 | Lee | A61B 5/6804 600/384 |
| 2016/0317067 A1* | 11/2016 | Lee | A61B 5/1118 |
| 2016/0349790 A1* | 12/2016 | Connor | G06F 1/1694 |
| 2017/0055573 A1* | 3/2017 | Utley | G16H 40/67 |
| 2017/0086741 A1* | 3/2017 | Bly | A61B 5/6826 |
| 2017/0095721 A1* | 4/2017 | Bleich | A63B 69/0028 |
| 2017/0164878 A1* | 6/2017 | Connor | A61B 5/14532 |
| 2017/0188864 A1* | 7/2017 | Drury | A61B 5/0408 |
| 2017/0312612 A1* | 11/2017 | Bleich | A63B 69/0028 |
| 2017/0348563 A1* | 12/2017 | Kim | G09B 5/02 |
| 2018/0020977 A1* | 1/2018 | Li | A61B 5/6826 600/384 |
| 2018/0042513 A1* | 2/2018 | Connor | A61B 5/6831 |

OTHER PUBLICATIONS

Figner, B. et al., "Skin Conductance I" "Using skin conductance in judgment and decision making research", In M. Schulte-Mecklenbeck, A. Kuehberger, & R. Ranyard (Eds.), A Handbook of process tracing methods for decision research. New York, NY: Psychology Press. 2010. pp. 163-184.

McEwen, B., "Allostasis and Allostatic Load: Implications for Neuropsychopharmacology", Neuropsychopharmacology 2000—vol. 22, No. 2. 1999. pp. 108-124.

Boucsein, W., "Electrodermal Activity", Second Edition, Springer Science+Business Media, LLC. 2012. Title page, and pp. 154-159.

* cited by examiner

BIOMETRIC WEARABLE FOR CONTINUOUS HEART RATE AND BLOOD PRESSURE MONITORING

CROSS-REFERENCE TO RELATED APPLICATIONS

This application claims priority to, and the benefit of, U.S. provisional patent application Ser. No. 62/528,336 filed on Jul. 3, 2017, incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to biofeedback devices, and more particularly to biometric wearables for short, medium, and long-term data acquisition and analysis applications.

2. Background Discussion

Electronic physiological monitoring equipment has long been available in various forms. Typically, these devices are configured for fulfilling a very specific and narrow role. For example, the electrocardiograph (ECG) is used to record the pattern of depolarization of the heart muscles as blood is pumped to the lungs for oxygenation and then out to all parts of the body. The ECG produces a pattern of electrical waves that are of diagnostic importance as related to heart function. Another specific device is the photoplethysmograph (PPG), which is well known in hospitals for quick assessment of heart rate based on sensing at the fingertip. A third specific device is used to measure electrodermal activity (EDA) which is a skin impendence measurement that indicates sympathetic nervous system (SNS) activation. However, these devices are generally directed to specific purposes in short term testing and not generally applicable for long term use and interaction with a user. In addition, the data from these separate devices are not combined to enable multichannel calculations.

BRIEF SUMMARY

Accordingly, the present disclosure overcomes the limitations of these short term discrete testing devices, while providing additional advantages.

The technology presented provides for placement of one or more biometric sensors on the finger, with the combination of sensor data allowing a determination of accurate assessments of the physiological state of the user within applications executing on a mobile device. A multichannel finger sensor system has been previously described by the Applicant as seen in U.S. Patent Application Publication No. US-2013-0183646-A1, which application and publication are incorporated herein by reference in their entireties.

In contrast to the above, the present disclosure describes a ring form factor with electronic provisions that allow for continuous monitoring of blood pressure, related SNS activity, and accommodation for different ring sizes. To produce quality biometric data, the biometric sensors must maintain proper skin contact on the finger. Toward that objective the present disclosure describes a sensor circuit that can fit within different sized rings, so that sensors are retained with proper skin contact and pressure.

Advantageously, various embodiments of the technology described herein may incorporate one or more of the following elements: (a) ECG, PPG, and EDA sensors whose data can be combined and correlated to assess the physiological state of the user; (b) mechanical innovation which allows for the construction of different ring sizes; and (c) inclusion of sufficient capacity energy storage (e.g., battery) to allow a user to wear the ring for extended periods of time (e.g., all day) which enables long term biometric data collection. This continuous data collection capability provides a new window on monitoring the ECG in real life situations.

The technology can be implemented with dedicated hardware, or for the sake of simplicity of implementation, may be executed using existing electronic devices. By way of example and not limitation, instructions of an application program (or programs) may be loaded for execution on a general purpose electronic processing device, such as a mobile device (e.g., smart phone, tablet, notepad, netbook, laptop, etc.). In at least one implementation, no additional hardware or hardware changes are required on the mobile device side. Thus, a user need only obtain the ECG, PPG, and EDA sensor device for streaming data to their mobile device, and the desired application to execute from that mobile device.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

1. Hardware Configuration

Figure 1:
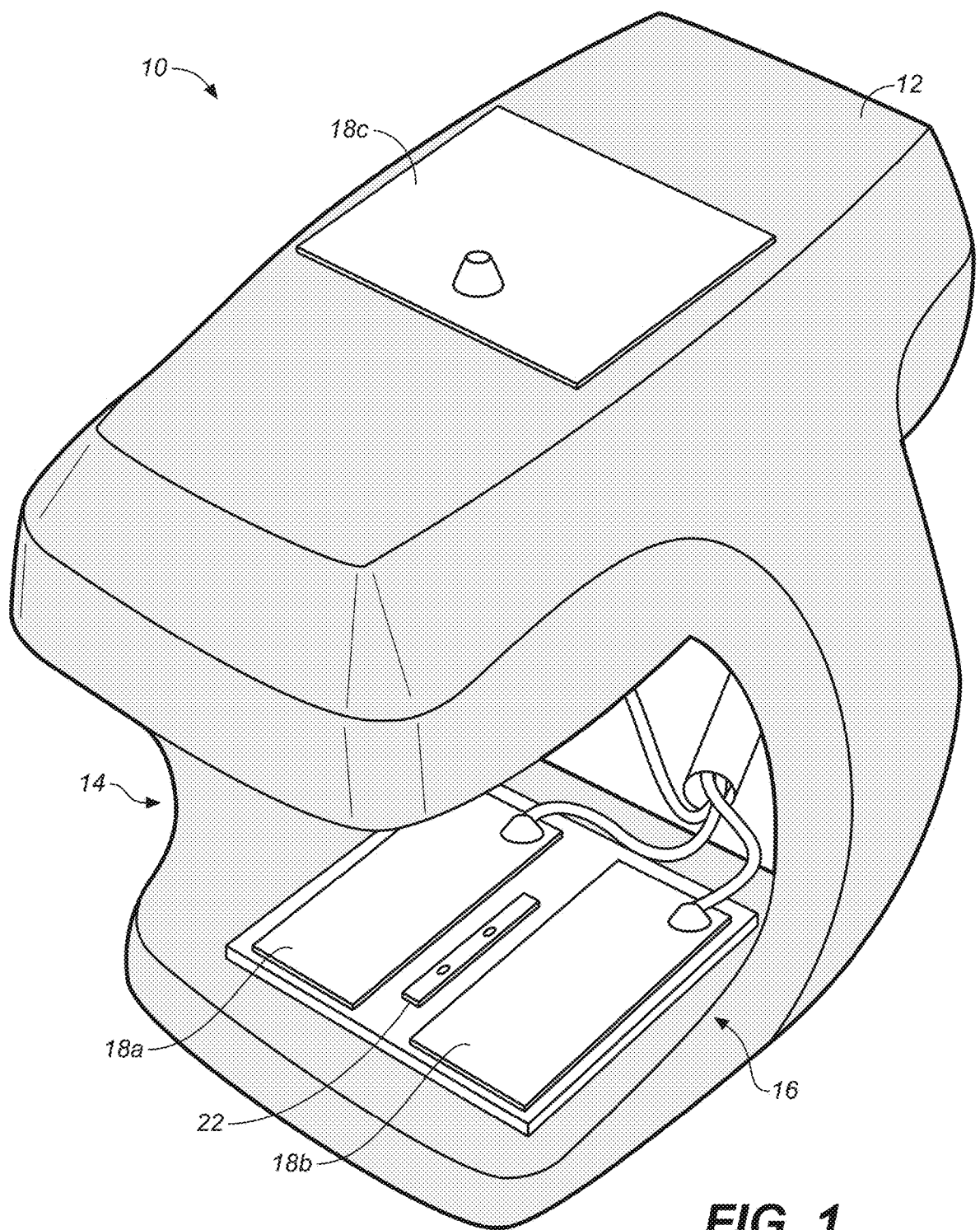
FIG. 1 shows a perspective image of an ECG capable ring with a three-electrode configuration according to an embodiment of the technology of this disclosure.

FIG. 1 shows a perspective view of a continuous wearable biometric sensing device 10 of the present disclosure that is configured to incorporate multiple sensor types. As shown in FIG. 1, device 10 includes three sensor types, that are disposed within a ring-shaped housing 12 having a finger aperture 14 so that the device 10 is wearable on any finger of a user's hand. The ring 10 comprises a plurality of sensor electrodes, with first and second sensor electrodes 18a and 18b disposed on an inner sensing surface 16 of aperture 14, and a third sensor electrode 18c disposed external to, or on an outer surface, of the housing 12.

Figure 2:
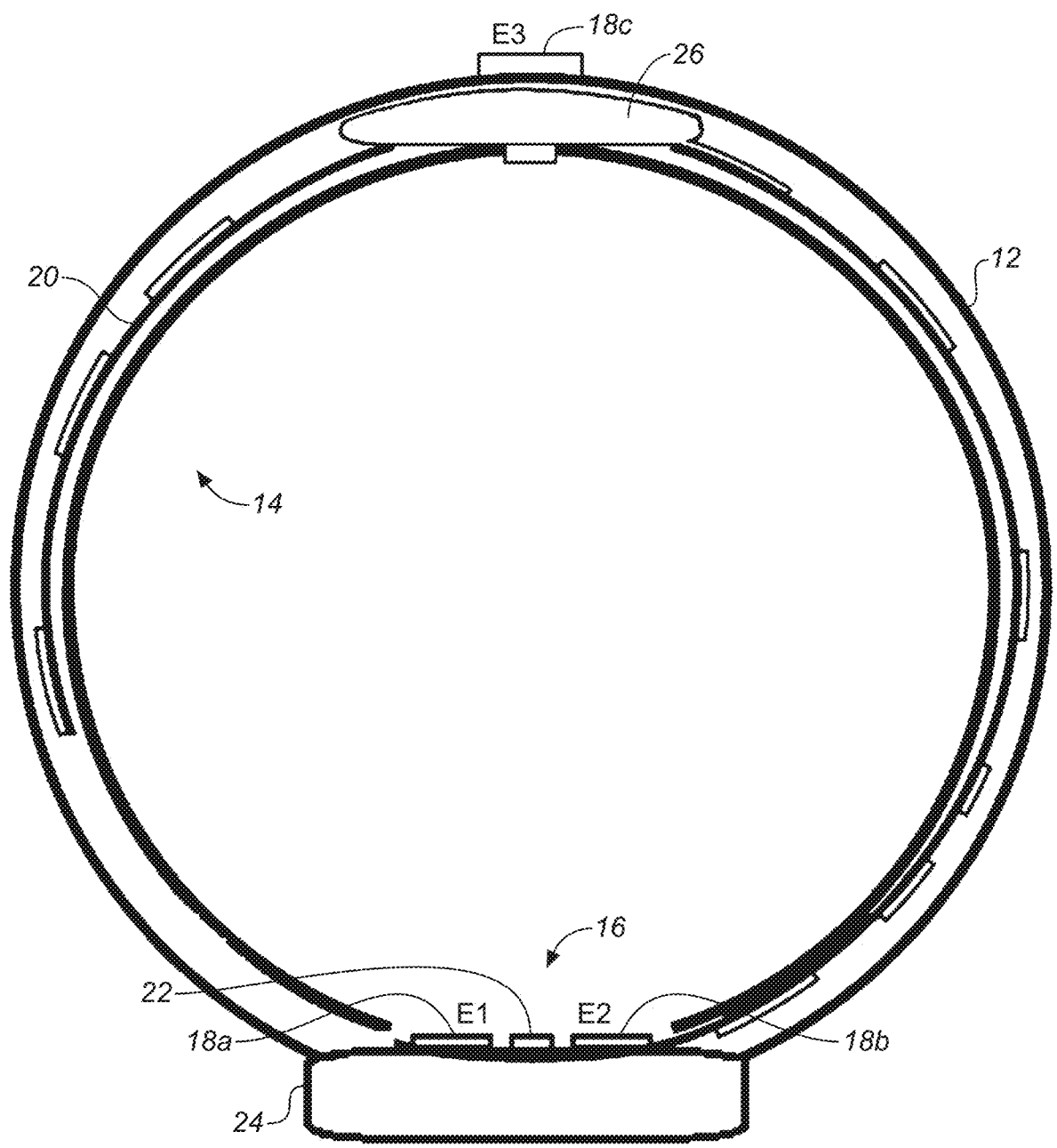
FIG. 2 is a cross-section of a ring in conformance with the embodiment of FIG. 1, having a flexible circuit board inside the ring.

Referring to the cross-section view of FIG. 2, a preferred embodiment comprises one or more of the sensors and associated hardware are contained on a flexible board 20 contained within the ring housing 12. The sensing ring can be worn on a finger in various ways, such as a ring worn on the third phalange (traditional ring position).

The ring body 12 is shown with sensor surface 16 exposed on an inner ring surface comprising ECG and EDA electrodes 18a and 18b that straddle a PPG (photoplethysmograph) module 22. Housing material 12 is shown on the exterior surrounding the flexible circuit board 20, upon which are connected various circuit elements (i.e. chips), and battery 24 are disposed. FIG. 2 also illustrates an alternative battery placement 26 that may be used instead of or in combination with battery 24.

2. Circuit Board and Sensor Surface

Figure 3:
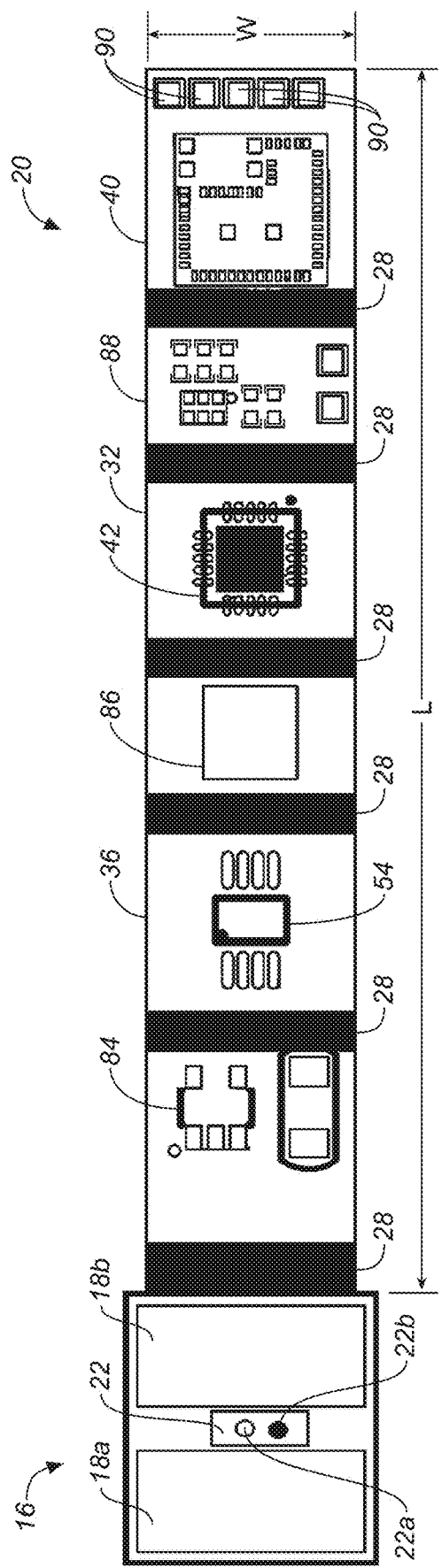
FIG. 3 is a schematic diagram of a flex board layout of the flexible circuit board of FIG. 2.

FIG. 3 shows an example embodiment of a sensor circuit comprising a multi-sensor circuit board 20. It is appreciated that any logic or circuitry for the device 10 (e.g. processor, op amps, memory, BLE module, battery, and passive components) are all preferably distributed along the board 20 to allow flex spaces 28 between the components. It is also preferable that the sensor surface 16 be mounted on the bottom interior of the ring aperture 14 to provide reliable contact with the skin of the palmar surface of user's finger (not shown). The configuration shown in FIG. 1 through FIG. 3 allows for a comfortable fit and also minimizes motion artifacts generated by skin/sensor movement.

FIG. 3 also shows a rigid sensor surface 16 extending from flex board 20, the sensor surface 16 comprising electrodes 18a and 18b for use with various sensors (e.g. ECG sensor 32 and EDA sensor 36 may both use comprising electrodes 18a and 18b sensor) along with PPG sensor 22. The flex board 20 also includes other various components, including but not limited to an instrumentation amplifier 42 for the ECG sensor 32, an instrumentation amplifier 54 for the EDA sensor 36, and a Bluetooth Low Energy (BLE) chip 40. The flexible substrate 20 fits inside of the ring enclosure 12 and is attached to the sensor surface 16.

In one embodiment, the PPG sensor 22 shown in FIG. 3 utilizes a green LED photo sensing emitter-receiver 22a/22b. Flex board 20 also includes an integrated accelerometer and gyro component 86, and 3V voltage regulator 84. Component section 88 comprises a series of passive components, where each horizontal pair of contacts comprises a surface mount for a resistor or capacitor. A series of programming connector contacts 90 is included for CPU boot loading and functions testing.

FIG. 2 illustrates an example of an average ring size (diameter). The flexible circuit board 20 may also be sized to have a length L and width W to fit in a smaller enclosure to accommodate a women's small size (e.g. 15 mm dia.) or in a larger enclosure to accommodate a men's large size (e.g. 22 mm dia.). The length of the flex section 20 of approximately L=42 mm and width W=7 mm (as shown FIG. 3) was found to accommodate this range of ring sizes.

Figure 4:
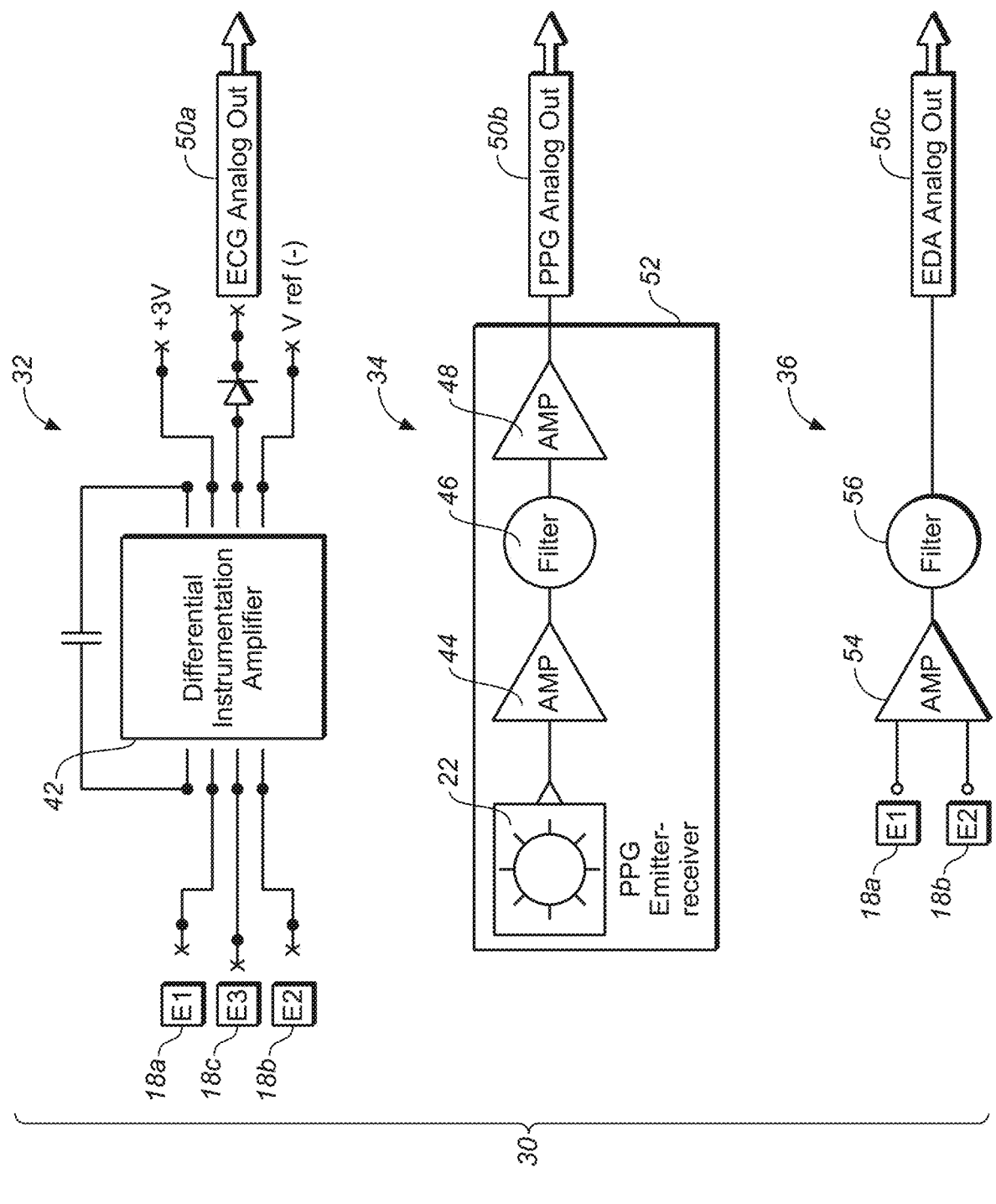
FIG. 4 is a schematic diagram of the sensor circuits used according to embodiments of the technology of this disclosure.

FIG. 4 is a schematic diagram of sensor circuit data capture and processing architecture 30 of the various sensors on the flex board 20. A series of inputs is shown, including an ECG sensor 32 that utilizes three electrodes (18a, 18b, and 18c) to register the electrical potentials from the heart muscle during contraction. This input circuit preferably incorporates a differential instrumentation amplifier 42 (e.g. AD8232) that provides large common mode noise rejection and high signal gain after the noise reduction phase. The ECG analog output 50a connects to the A/D input of the BLE integrated BLE processor 40, as shown in greater detail in FIG. 5.

Also shown in FIG. 4, an EDA (electrodermal activity) sensor 36 is provided to measure an EDA signal generated from electrodes E1 and E2 (18a and 18b) that register changes in skin resistance. The signals are amplified with a second instrumentation amplifier 54 (separate from the ECG circuit) and low pass filter 56 to minimize 60 Hz environmental electrical noise that are integrated on the EDA sensor 36 (e.g. INA156 instrumentation amp). The EDA sensor 36 may measure user SNS activation in order to correlate changes in blood pressure with autonomic nervous system influence on heart rate. In a preferred embodiment, the EDA electrodes 18a and 18b contact the palmar side of the finger where there is the greatest density of eccrine sweat glands that respond to SNS activation. The analog EDA signal 50c inputs to an A/D input 62c on the integrated processor 40 as shown in FIG. 5.

FIG. 4 also illustrates PPG sensor 34 (e.g. Si1144 integrated PPG module), which utilizes a green LED photo sensing emitter-receiver 22 (e.g., sensitive photo-transistor) that produces a small voltage with green light illumination. Blood perfusion in the finger produced by cardiac pulse causes the green light to be scattered and thus the light detector's output varies with pulse. The green light signal is amplified and filtered with amplifiers 44, 48 and filter 46, before outputting a light varying analog signal 50b to the processor A/D 62b input shown in FIG. 5.

An auxiliary A/D input 62d may also be included to receive auxiliary input 50d from one or more auxiliary devices, e.g. 3D motion data, temperature data, or chemical assay data from an accelerometer, thermistor, or nanotube array (all not shown) respectively.

Figure 5:
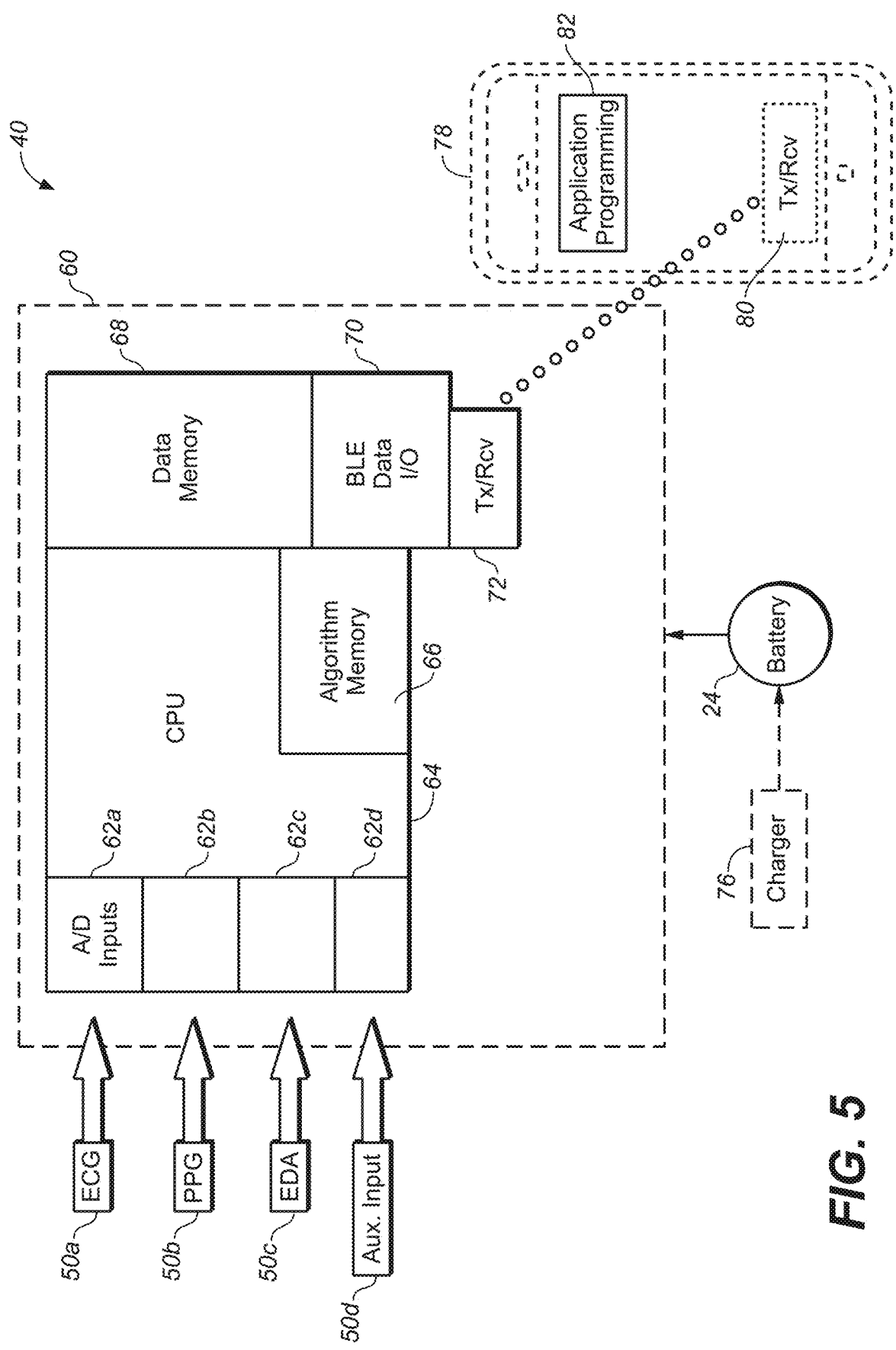
FIG. 5 is a schematic diagram of biometric ring circuit architecture according to an embodiment of the technology of this disclosure.

As illustrated in the integrated BLE processor 40 shown in FIG. 5, the inputs 50a, 50b, 50c and 50d are received at respective inputs 62a, 62b, 62c and 62d, and then preferably conditioned, typically including amplification and/or filtering, followed by conversion to a digital signal, such as by an analog-to-digital converter, prior to receipt by a processing unit 64 (e.g., CPU, microprocessor, microcontroller, DSP, or one or more electronic devices configured to process the sensor signals). Instructions for execution by the processor (or processors) and data, are stored in one or more memories (e.g. algorithm memory 66). The CPU 64 runs signal processing methods for analyzing features of the multi-sensor data stream. Results of signal processing and raw data itself can be stored in the data memory 68. The above-mentioned components, along with BLE data I/O module 70 and wireless transmission/receiver module 72 may all be integrated on one logic device 60 (e.g. BCM121 integrated BLE processor).

It will also be appreciated that the computer readable media (memory storing instructions) in both the biometric sensor ring 10 and external applications to which it communicates, are computation systems with memory that are "non-transitory", that is to say they may comprise any and all forms of computer-readable media, with the sole exception being a transitory, propagating signal. Accordingly, the disclosed technology may comprise any form of computer-readable media, including those which are random access (e.g., RAM), require periodic refreshing (e.g., DRAM), those that degrade over time (e.g., EEPROMS, disk media), or that store data for only short periods of time and/or only in the presence of power, with the only limitation being that the term "computer readable media" is not applicable to an electronic signal which is transitory.

By way of example and not limitation, at least one embodiment of the instruction programming (e.g., firmware) is configured for scanning the ECG sensor at 200 Hz, the PPT sensor at 50 Hz, and the EDA at 20 Hz with voltage level data streamed to application programming which executes on a remote device, preferably a smart phone. It is appreciated that the sampling rate is programmable for each sensor channel, and sampling rate (SR) may be set to other values. For example, in some cases 1 kHz may be used for high quality ECG. In one embodiment the BLE module contains the firmware memory, although various other memory configurations can be utilized without departing from the present disclosure. Embodiments of the application programming for smart phones have already been developed for iOS and Android operating systems. This application which executes from the smart phone can perform a wide variety of biosensing data collection, analysis, and display functions. For example, one embodiment of firmware records a time stamp, records ECG level every 5 msec, records EDA level every 20 msec, and records PPT level every 100 msec, determines and records instantaneous heart rate (HR), average HR, and HR variability.

The input gains are adjustable depending on the level of the input sensor signal, which can vary more than a factor of 100 (100 uV for EDA versus 10 mV for ECG), so the input stage is shown configured to scaling for these large differences. The analog signals are converted to digital signals in the processor A/D (analog to digital converter). The sampling rate of each channel can be independently set depending on the bandwidth of the input signal.

A wireless communication protocol is also supported as exemplified with BlueTooth Low Energy (BLE) device 70 comprising or coupled to a transmitter/receiver 72 shown for wirelessly communicating with Tx/Rcv 80 of another electronic device 78 (e.g. smart phone or the like), which can allow for controlling device operation, registering collected sensor data, analyzing collected data, displaying collected data or analyzed data, or any combination thereof. It is appreciated that the BLE module 70 may contain the radio (Tx/Rcv) 72, wherein there is no need for the separate Tx/Rcv 72 shown in FIG. 5. Data can be uploaded to an external network at any time, such as via the exemplified BLE I/O module 70. The BLE module 70 utilized in the example embodiment may contain its own processor and memory and can be configured for different types of network protocols aside from the BlueTooth protocol. New signal processing algorithms can be downloaded to program memory in the CPU 64 via the BLE module 70. In one implementation, the BLE module 70 may contain the ND inputs, processor, memory (e.g., instruction programming, firmware), transmit/receive radio, and antenna.

A self-contained power source, exemplified as a battery 24, is shown for powering the ring sensing device 10, and is shown with an optional charger 76, thus allowing the user to move about during the course of their normal activities.

Figure 6A:
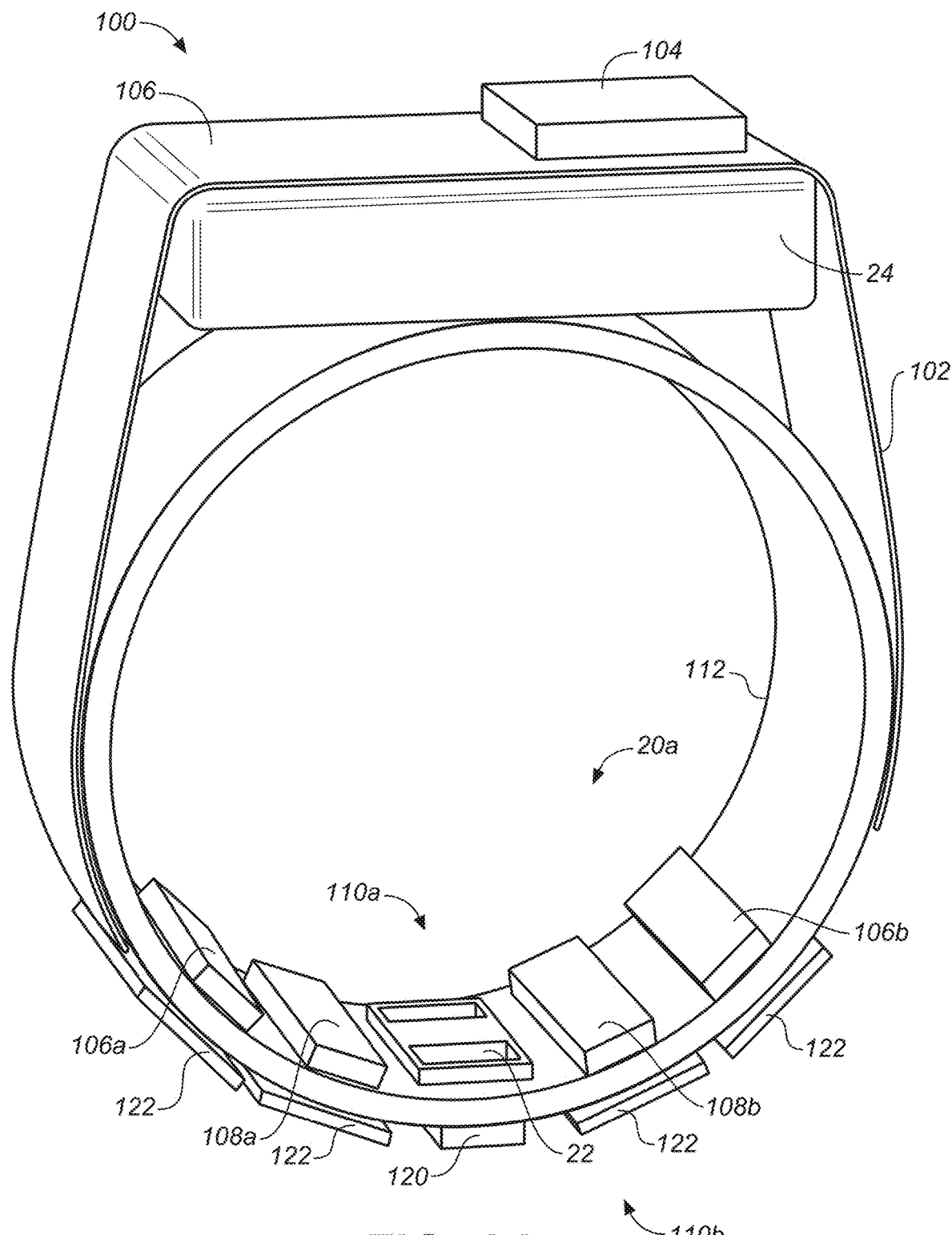
FIG. 6A shows a perspective image of an alternative embodiment of an ECG capable ring in accordance with an embodiment of the technology of this disclosure.

FIG. 6A illustrates an alternative continuous wearable biometric sensing ring 100 embodiment having a ring enclosure 102 with the flex board 20a disposed within (the outer part of the ring enclosure 102 is removed in FIG. 6A for visibility). In this embodiment, the BLE module 104 and battery 24 are disposed in the top area of the ring 100. The BLE may also be on the flex board 20a (as detailed in FIG. 6 showing BLE processor 40). Also, separate pairs of ECG electrodes (106a, 106b) and EDA electrodes (108a, 108b) are shown straddling opposite sides of PPG module 22 on the bottom interior sensing surface 110a of the aperture of the ring 100 (is generally of the shape of the flexible board substrate 112). This is distinct from the configuration of FIG. 1 and FIG. 2 which show the EDA and ECG sharing the electrodes. On the opposite side of the flex board 20a (in between circuit component chips 122), a third ECG electrode 120 (which in one configuration comprises a gold-plated copper block) is positioned so that it has a free sensing surface 110b that protrudes through the shell of the ring enclosure 102 (not shown) to allow for contact with a contralateral side of the body.

It should be appreciated that the processor, op amps, memory, BLE module, battery, and passive components (all not shown) are all preferably distributed along the board 20a to allow flex spaces between the components. It is also preferable that the sensor surfaces be mounted on the bottom interior of the ring to provide reliable contact with the skin of the user's finger. Ring enclosure 102 may also comprise an antenna 106 (e.g. Bluetooth or the like) comprising a trace at the upper location of the ring 100.

Figure 6B:
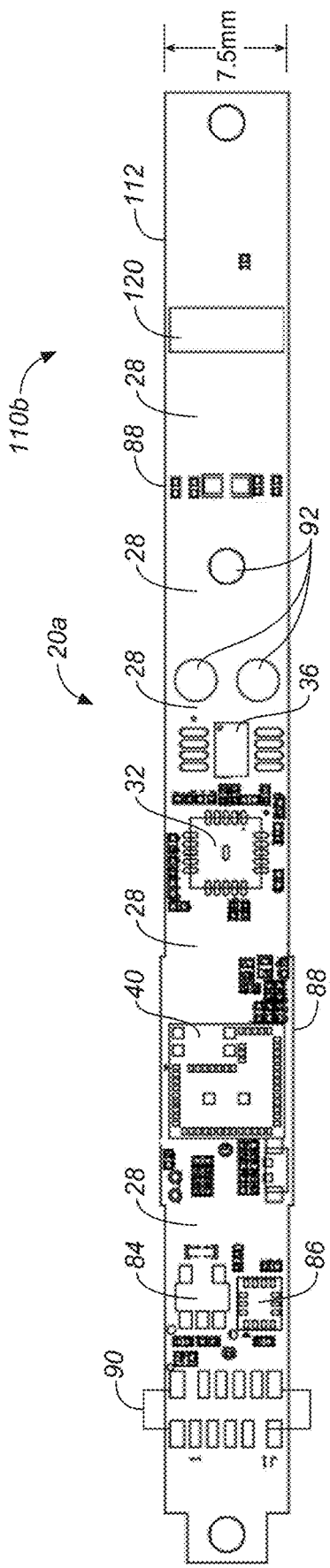
FIG. 6B shows a top-view schematic diagram of a flex board layout of the flexible circuit board of the device of FIG. 6A.
Figure 6C:
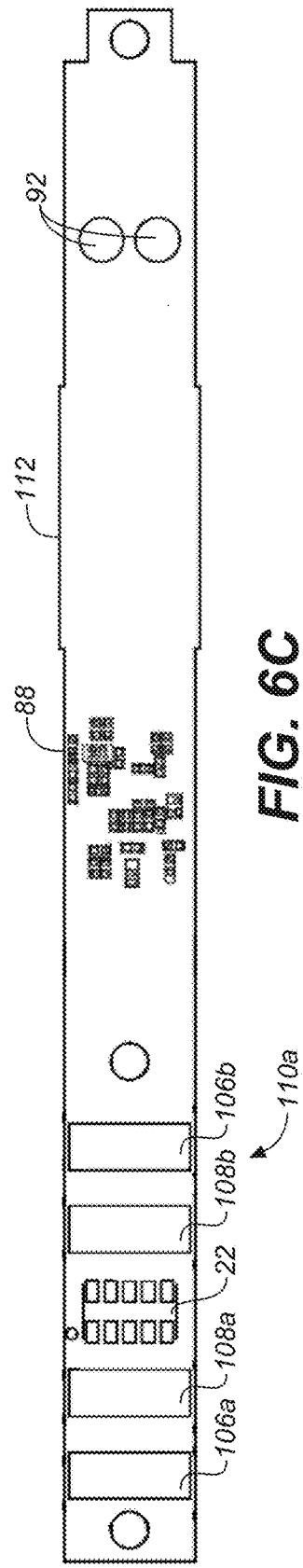
FIG. 6C shows bottom-view schematic diagram of a flex board layout of the flexible circuit board of the device of FIG. 6A

FIG. 6B and FIG. 6C show a top-view and bottom-view, respectively, of a flex board layout of the flexible circuit board 20a that may be used for ring 100 of FIG. 6A. It is also appreciated that this configuration of flex board 20a may be used for other device configurations that are not ring-based. While the ring configuration, and corresponding finger contacts, provide a preferred configuration for establishing primary and contralateral contact with the skin, it is appreciated that other shaped configurations are also contemplated. For example, the flex board 20a may be implemented as a patch (not shown) that may be adhered to the surface of the skin so that the inner sensing surface 110a contacts the skin at the attachment location (e.g. arm, back of hand, chest etc. and the second (outer) sensing surface 110b is able to contact a contralateral location of the body (e.g. opposite finger, neck, etc.)

Referring to FIG. 6B and FIG. 6C, the interior sensing surface 110a comprises pairs of ECG electrodes (106a, 106b) and EDA electrodes (108a, 108b) that straddle opposite sides of PPG module 22 on the flexible substrate 112, along with passive components 88 and battery charger contacts 92 (FIG. 6C). On the opposite side (FIG. 6B), the flex board 20a comprises third ECG sensor 120 for second (outer) sensing surface 110 b, and other various components disposed between flex areas 28, including but not limited to an instrumentation amplifier for ECG sensor 32, an instrumentation amplifier for the EDA sensor 36, a Bluetooth Low Energy (BLE) chip 40, 3V voltage regulator 84, integrated motion unit (IMU) 86. Passive component sections 88 comprise a series of passive components, where each horizontal pair of contacts comprises a surface mount for a resistor or capacitor. A series of programming connector contacts 90 is included for CPU boot loading and functions testing.

In one configuration for a ring embodiment, the length of the flex board 20a is approximately 96 mm, with a width of 7.5 mm. It is appreciated that the flex board may comprise any number of shapes and sizes (e.g. for a wearable patch configuration (not shown), the flex board may be more square (or less rectangular) based on the desired location of adhesion.

3. Biometric Signal Processing

As detailed above, the biometric ring 10/100 is configured to send sensor data to a mobile device 78, such as through the BLE interface 70, to be decoded in the mobile device application programming 82 configured to process the data on the mobile device processor to: (a) display information in a raw data form (e.g., graphing routine); (b) analyze (process) the information and display average values, time related values, threshold related values, emotional state charts/plots/indicators; (c) display animations to depict the raw and/or analyzed sensor information; (d) utilize the raw and/or analyzed data within a game or other application utilizing the emotional estimations as part of its received information (e.g., application 82 may also take inputs from keyboards, pointing devices, mobile device motion sensing, mobile device position (i.e., GPS), etc.).

a. Blood Pressure (BP) Calculation

According to at least one embodiment of the technology described herein, ring device 10 comprises a continuous blood pressure monitor comprising an ECG sensor 32 for measuring the electrical signature of heart muscle depolarization. The sensor 32 comprises three electrodes (E1, E2, and E3 in FIG. 1)—two that contact the bottom side of the finger on the inside surface of the biometric ring, and the third on the outside surface of the ring that is contacted by a finger of the opposite hand as shown in FIG. 2. The ECG sensor is used to derive user cardiac electrical activity and is temporally compared to the pulse from the PPG sensor in the ring.

In one embodiment, the ECG sensor utilizes the third electrode 18c in a manner in which it is positioned on the bottom of the ring, e.g. oriented in a palmar-facing position. This ring configuration allows the user to touch several points on the opposite side of the body in order to acquire the ECG signal. ECG signal acquisition is possible from many locations on the contra-lateral side of the body. For example, the ring 10 may be worn on the left hand so that the third electrode 18c can contact the clavicle on the right side of the user. In another embodiment, the ring 10 may be positioned with ECG recording position facing dorsal with respect to the hand of the user, with the opposite finger touching the third electrode 18c.

Figure 7:
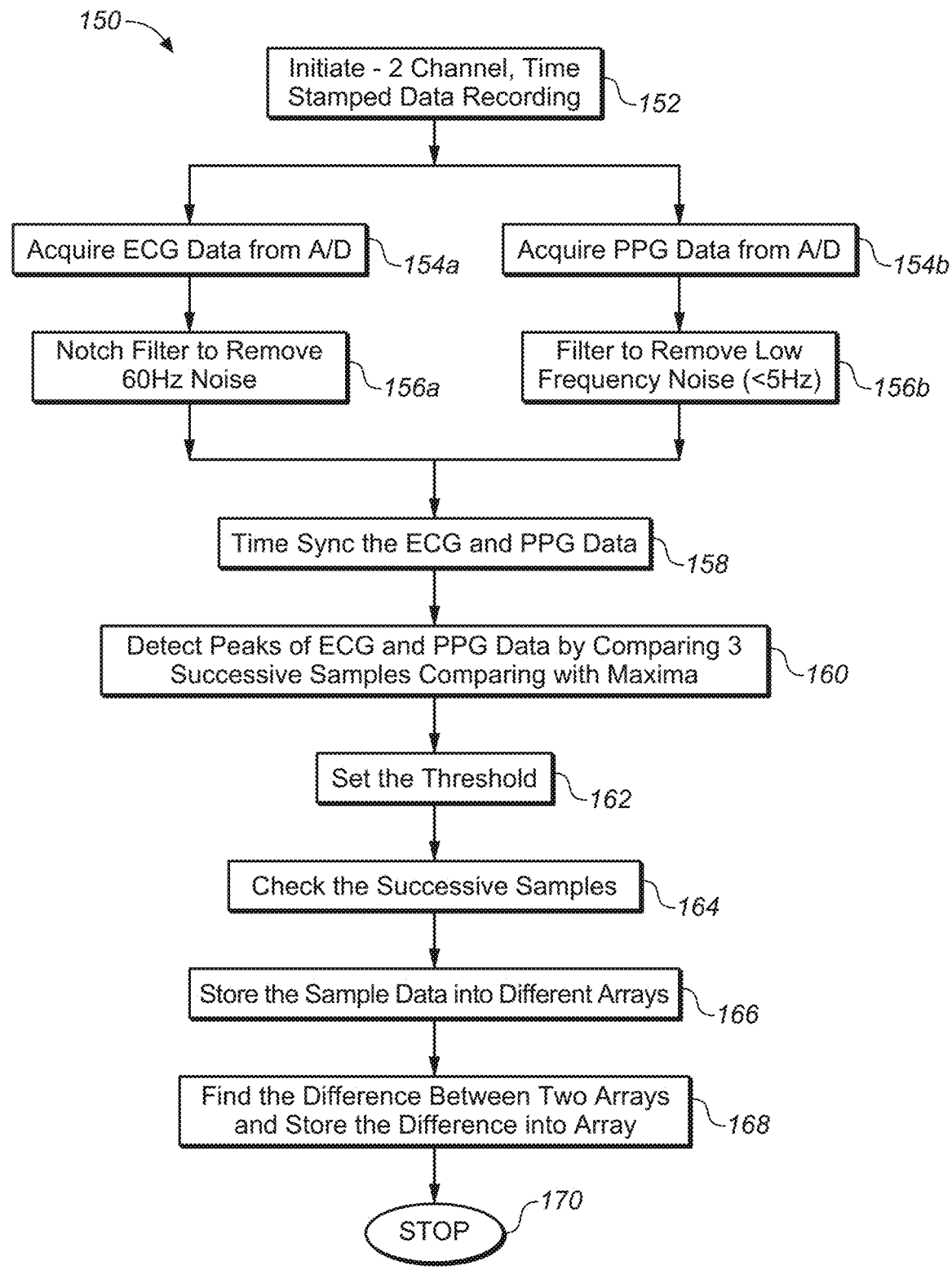
FIG. 7 is a flow diagram illustrating ECG and PPG peak picking and PTT derivation according to an embodiment of the technology of this disclosure.
Figure 8:
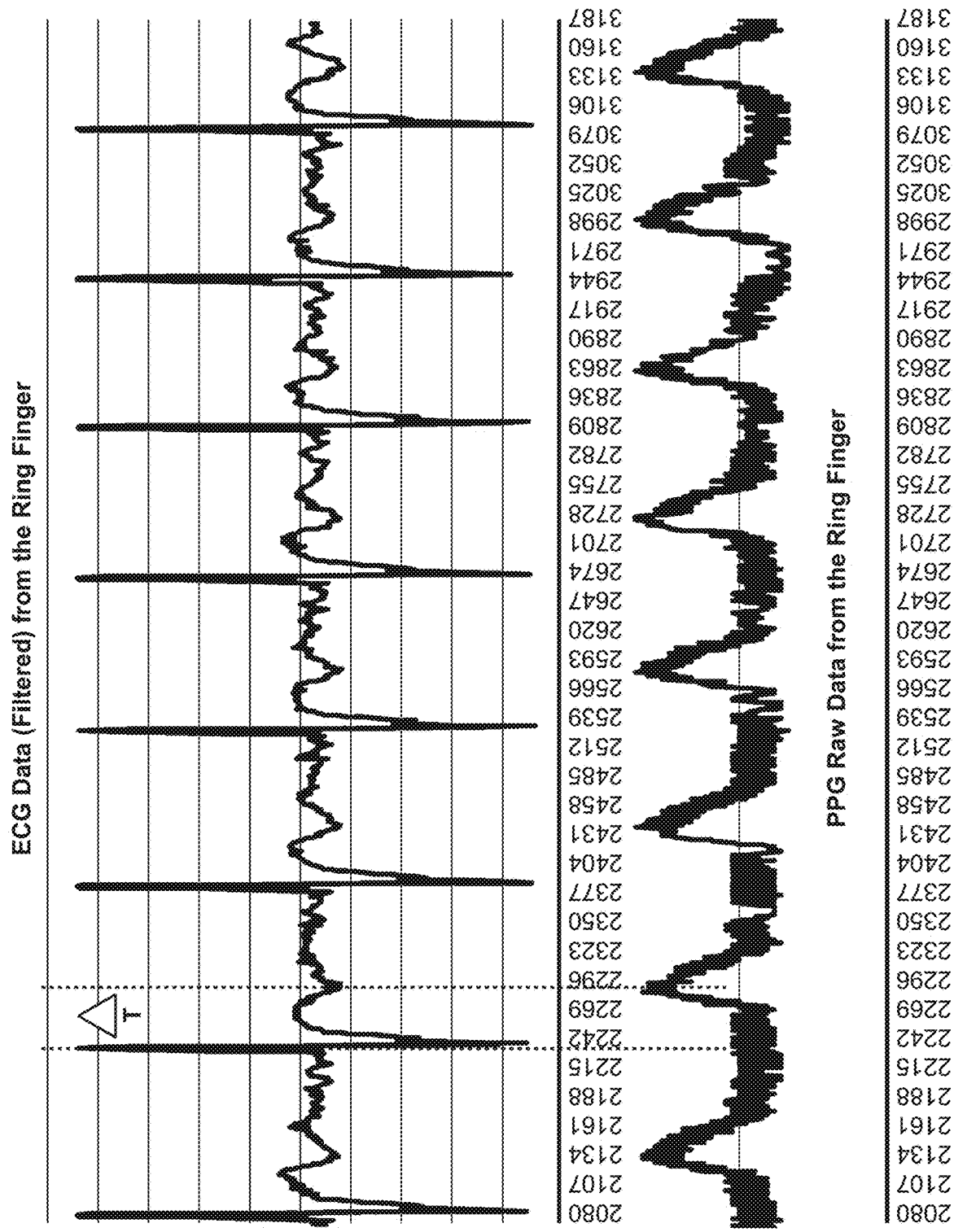
FIG. 8 shows ECG and PPG data channels illustrating pulse transit time according to an embodiment of the technology of this disclosure.
Figure 9:
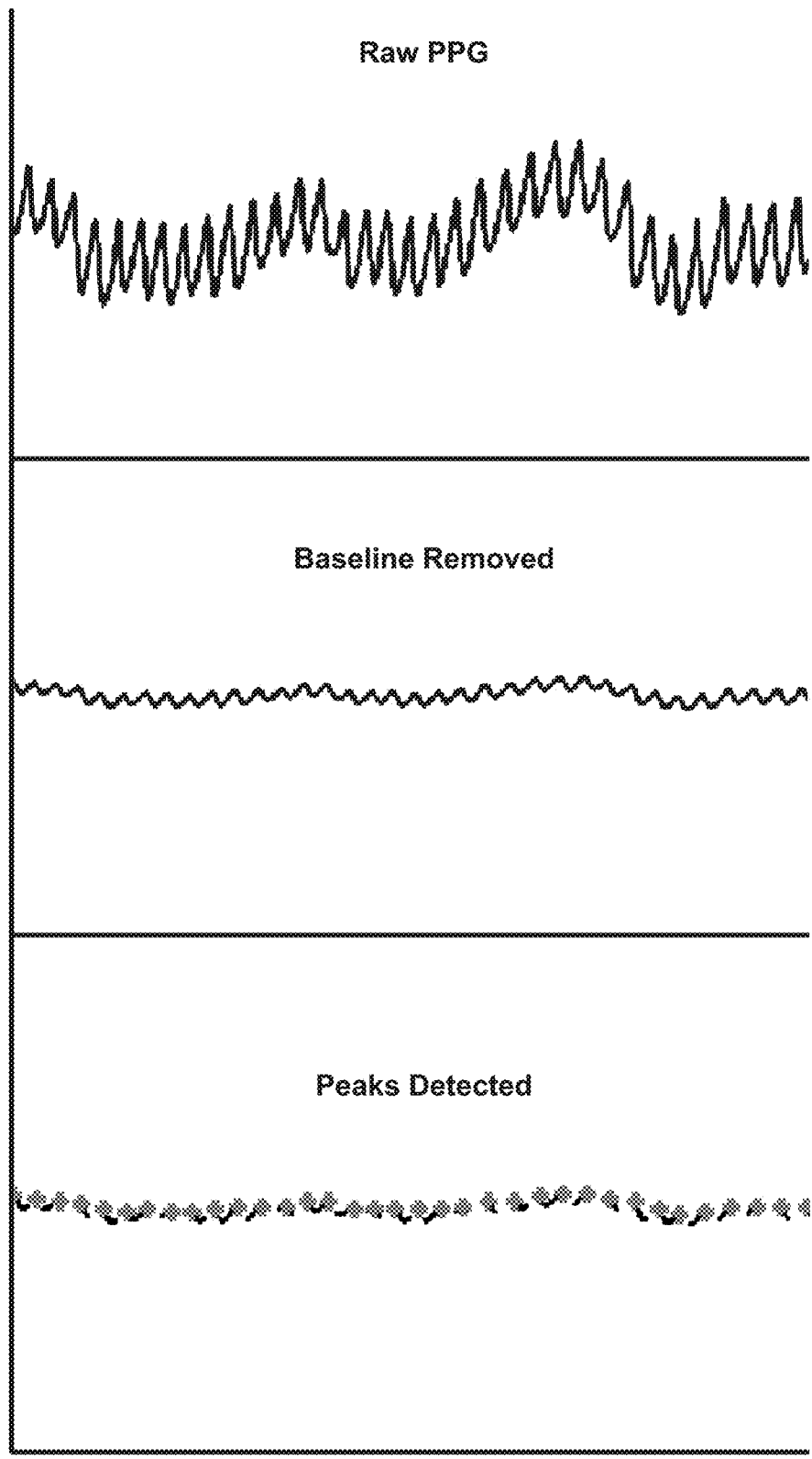
FIG. 9 illustrates steps used in a peak picking algorithm according to an embodiment of the technology of this disclosure.

In a preferred embodiment illustrated in FIG. 7 through FIG. 9, biometric ring data from the ECG 32 and PPG 22 sensors is used to calculate blood pressure continuously by the pulse transit time (PTT) method, as the PPG sensor 22 provides functionality for measuring user cardiac pulse. Various types of calculations for the PTT method may be used, but the essential element that these calculations have in common is the use of both ECG 32 and PPG 22 sensor data. Generally, the ECG data is derived from standard adhesive electrodes attached to the chest, and the PPG data is recorded from sensors on the arm, wrist, or finger. The time difference between the R wave peak in the ECG (from the QRS wave complex) and the peak of the PPG wave is utilized as the PTT interval and forms the basis of the blood pressure calculation.

FIG. 8 illustrates the PTT between the ECG wave peak and the PPG wave peak labeled as delta T between the dotted lines. The ECG and PPG channels were recorded simultaneously from the ring with the sample number for each channel shown below the data plot. One particular novel advantage of the biometric ring 10 of the present description lies in combining the ECG 32 and PPG 22 sensors in one device in order to provide a continuous PTT measurement.

FIG. 7 shows a schematic flow diagram detailing an exemplary computational method 150 for deriving blood pressure, both systolic and diastolic. The method involves: 1) finding the peaks of the ECG and PPG waves; 2) calculating the time difference between the ECG peak and PPG peak to derive the PTT; 3) calibrating a set of PTT measurements against standard BP measurements to determine the individual's variance (from the standard measure) due to height and weight. FIG. 9 shows an example peak picking process for PPG data from the ring sensor. The data is first high pass filtered to minimize the low frequency fluctuations, then the peak detection code using a moving average window looks for a change from positive to negative, and then checks that the size of the change against a set threshold.

Referring to FIG. 7, the method 150 starts by initiating 2-channel, time-stamped data recording at step 152. Next, the method acquires ECG data and PPG data from A/D at steps 154a and 154b, respectively. A notch filter is applied to the acquired ECG data to remove 60 Hz noise at 156a, and a filter is applied to the acquired PPG to remove low frequency noise (<5 Hz) at step 156b. At step 158, the ECG and PPG data is time synced.

At step 160, the method detects the peaks of the ECG and PPG waves by comparing 3 successive samples with maxima. A threshold is set at step 162, and then successive samples are checked at step 164. The sample data is then stored into different arrays at step 166. The difference between the two arrays is then calculated at step 168, where the routine ends at step 170.

b. Heart rate (HR) and Heart Rate Variability (HRV) Calculation

HR is calculated from the ECG 32 and PPG 22 sensors by using the peak picking routine of FIG. 7, and then measuring the inter-beat interval (IBI). The instantaneous HR is derived from every IBI and the average HR is calculated by averaging the IBI over n beats. This analysis system allows for a variable n so the user can change the IBI averaging window cases. Generally, a higher HR over a period of minutes in the absence of physical exercise corresponds to SNS activation and can be associated with a BP increase. A reduction in HR corresponds to parasympathetic nervous system (PNS) activation associated with relaxation and BP decrease.

HRV is calculated from HR from the ECG 32 and PPG 22 sensors over a specified number of IBI intervals. HRV is the standard deviation of the HR during a specified time interval—preferably when the user is sitting or lying quietly for 5 minutes. The HRV calculation derived from ECG is superior to HRV derived from PPG since the ECG R wave is temporally much sharper than the PPG pulse wave. This gives the HRV from ECG millisecond accuracy which can reflect precision changes over time when evaluating stress interventions—such as daily meditation, dietary changes, or daily exercise.

Figure 10:
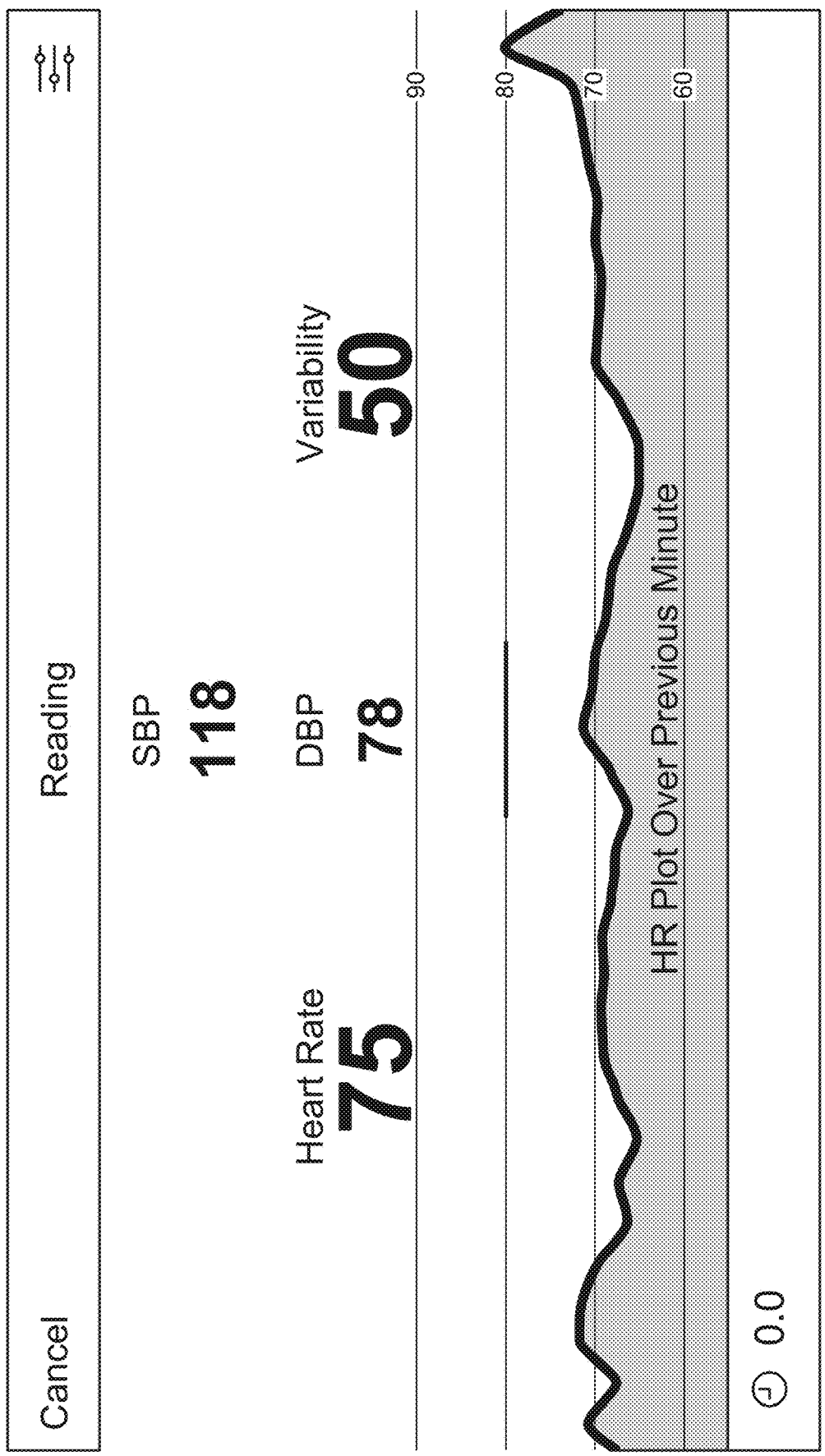
FIG. 10 illustrates an exemplary application screen showing HR, HRV, and BP values according to an embodiment of the technology of this disclosure.
Figure 11:
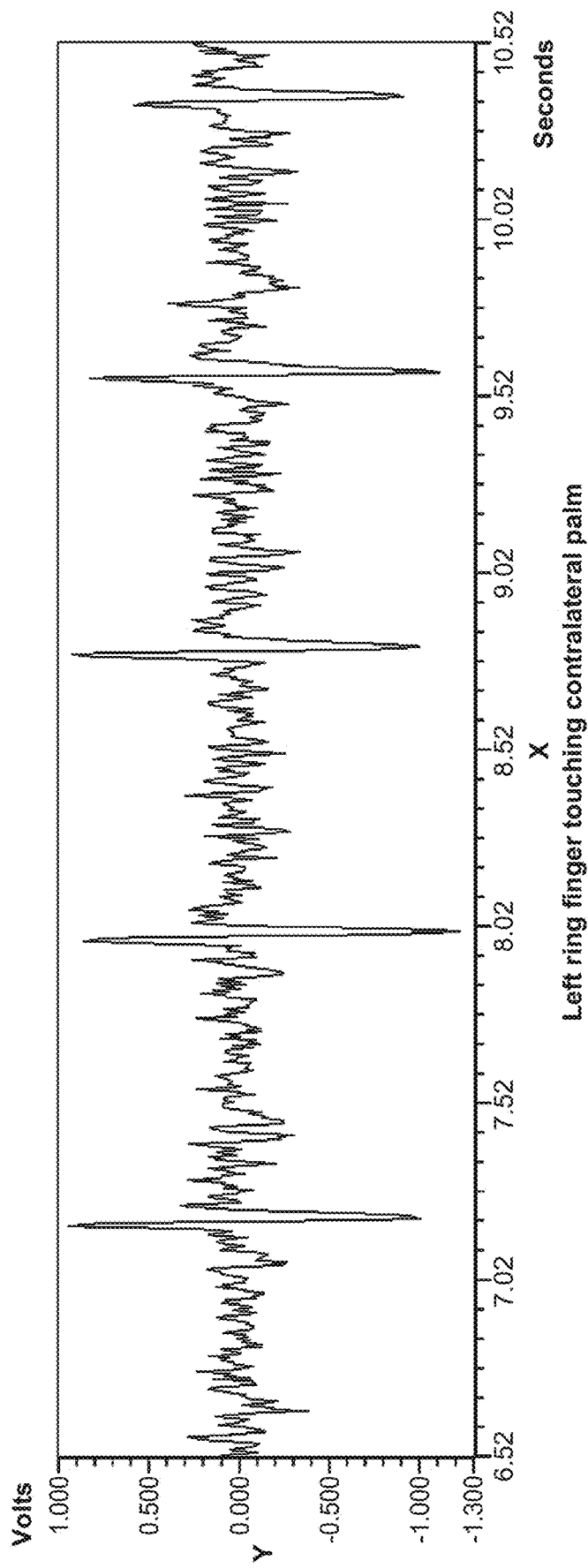
FIG. 11 shows an ECG series plot with the ring on the left hand with the external ring electrode contacting the contralateral palm.
Figure 12:
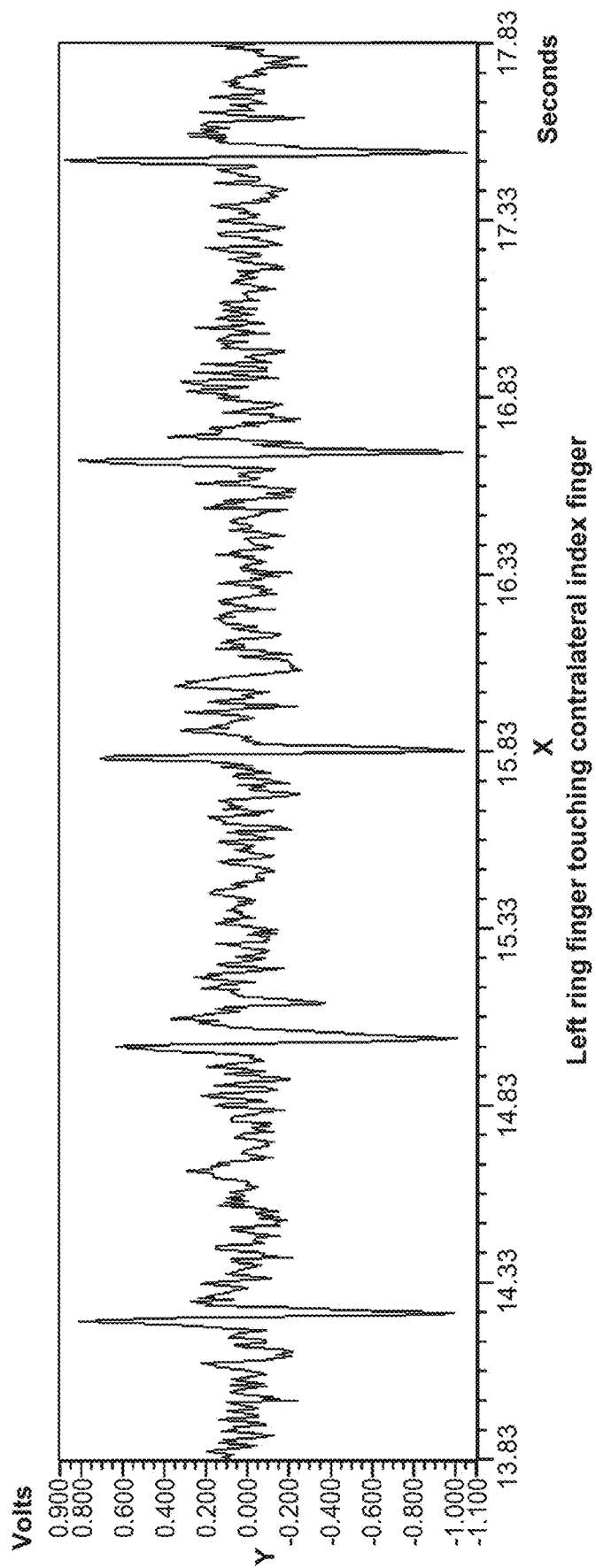
FIG. 12 shows an ECG series plot with the ring on the left hand with the external ring electrode contacting the contralateral index finger.
Figure 13:
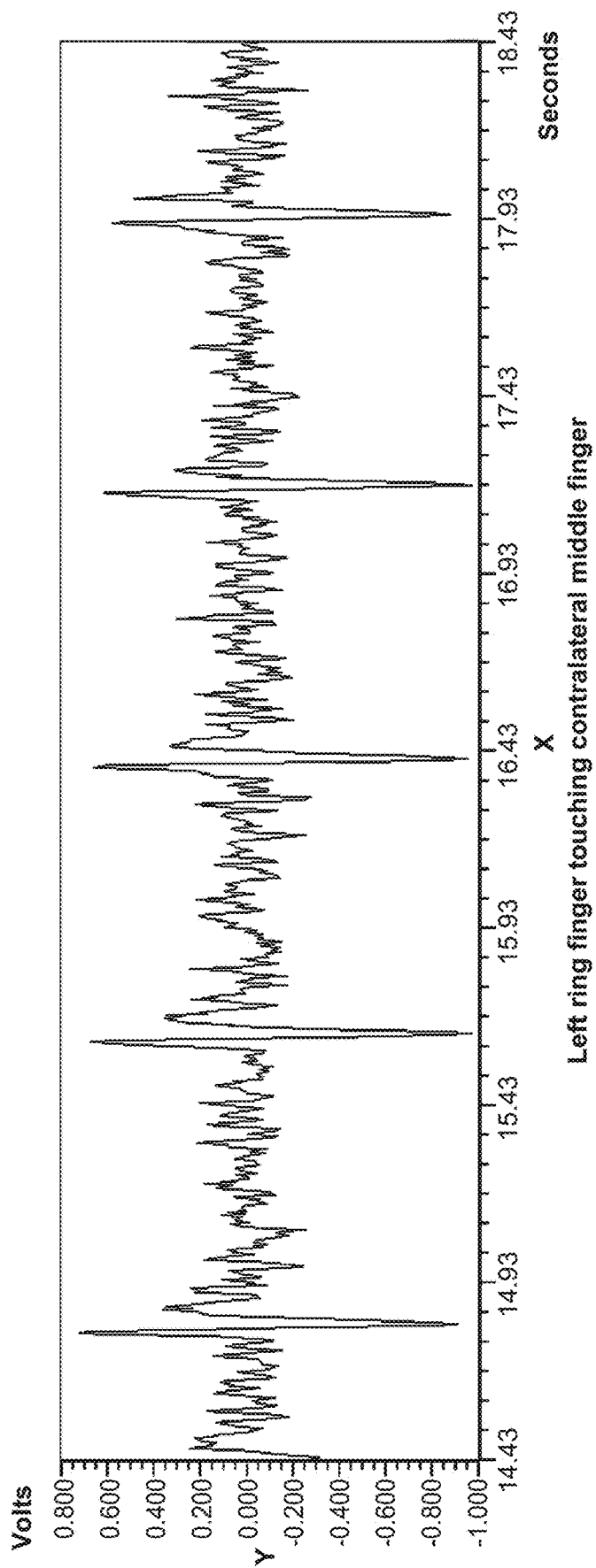
FIG. 13 shows an ECG series plot with the ring on the left hand with the external ring electrode contacting the contralateral middle finger.
Figure 14:
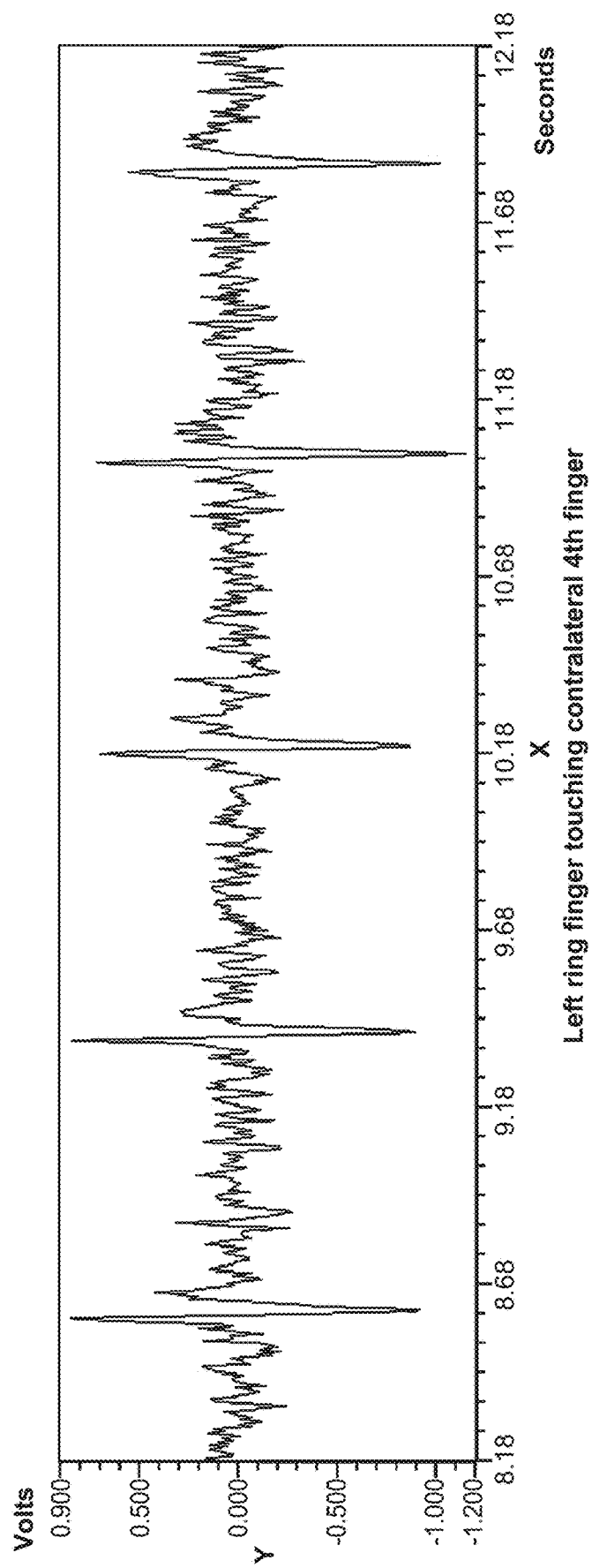
FIG. 14 shows an ECG series plot with the ring on the left hand with the external ring electrode contacting the contralateral 4th finger.
Figure 15:
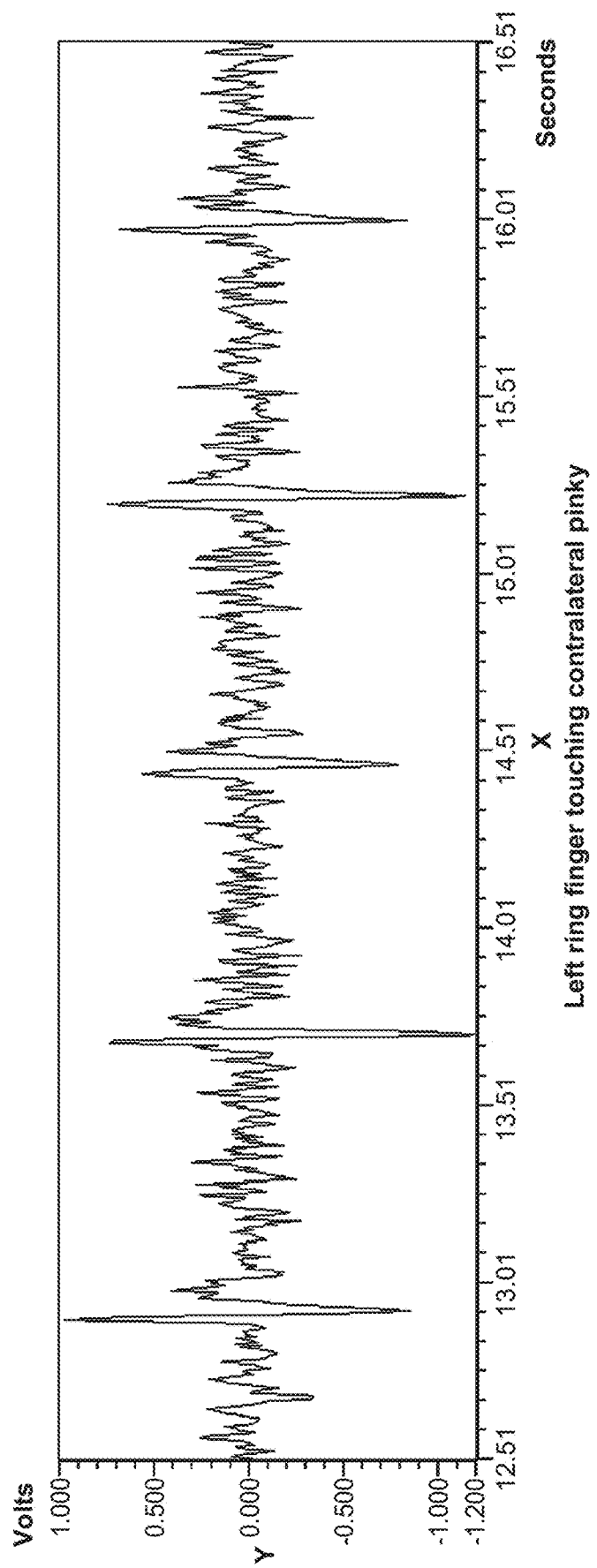
FIG. 15 shows an ECG series plot with the ring on the left hand with the external ring electrode contacting the contralateral pinky finger.
Figure 16:
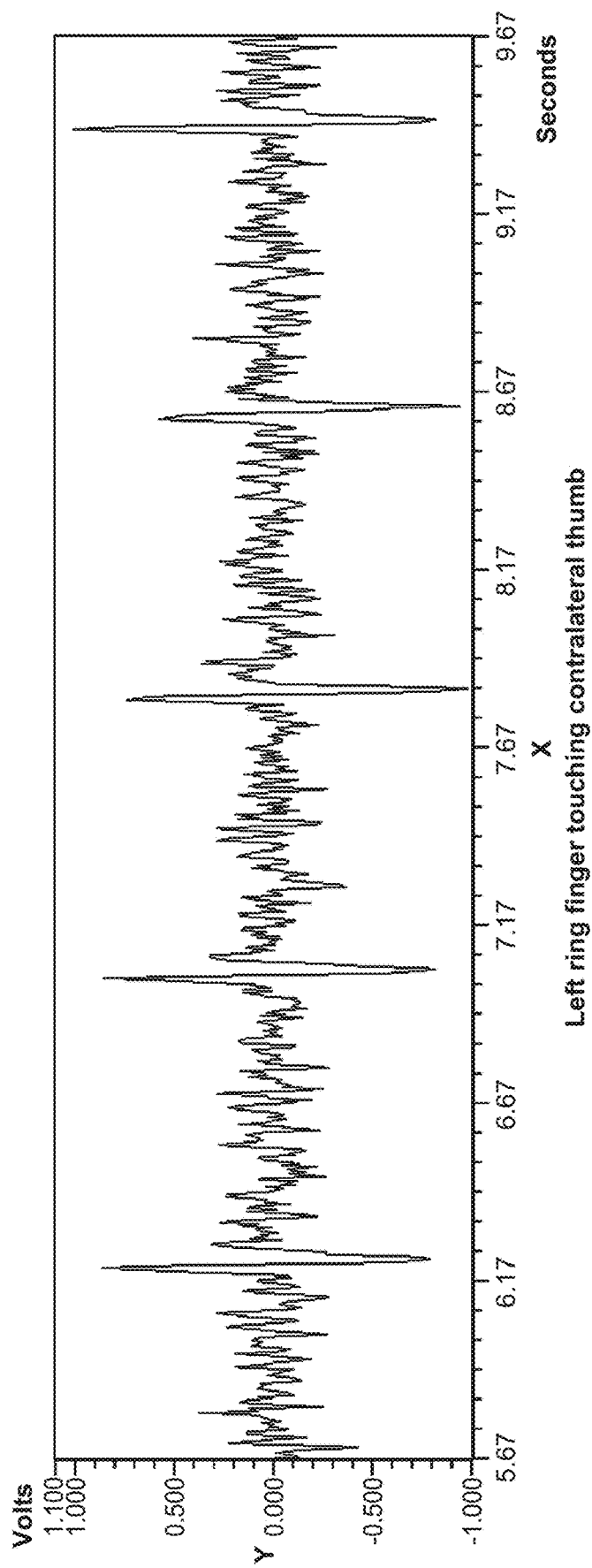
FIG. 16 shows an ECG series plot with the ring on the left hand with the external ring electrode contacting the contralateral thumb.
Figure 17:
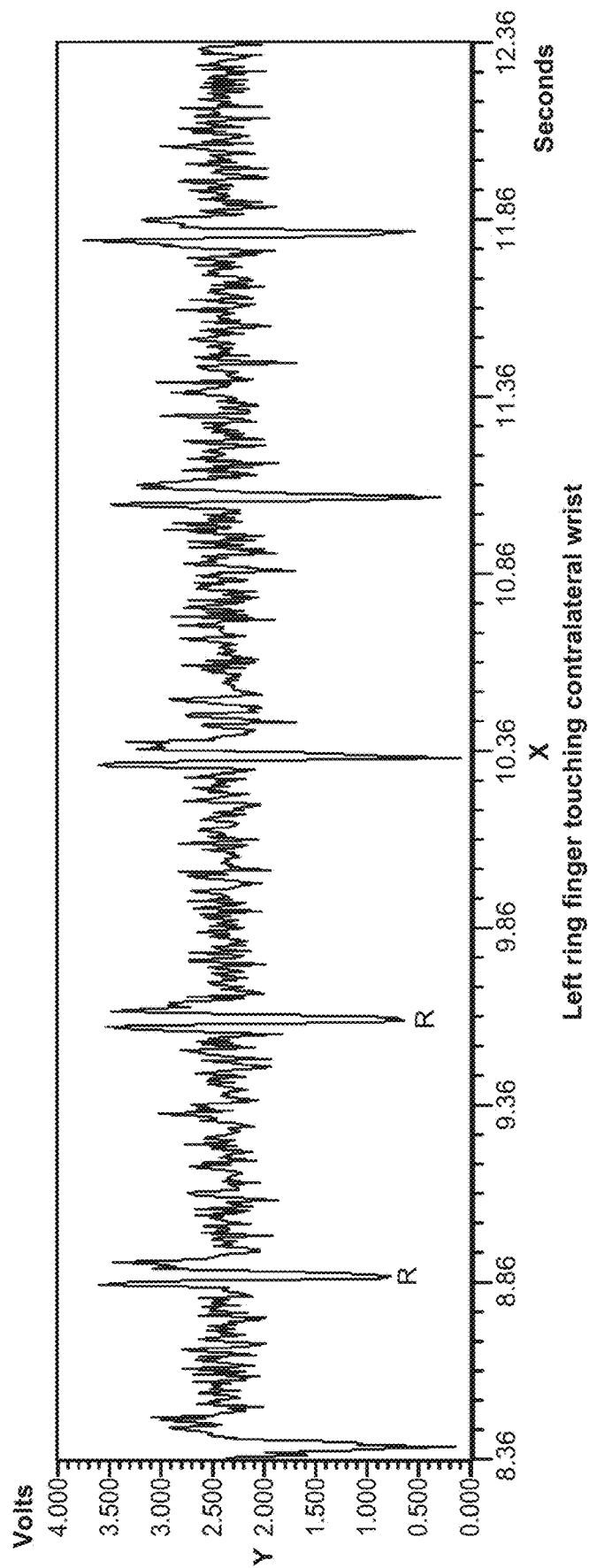
FIG. 17 shows an ECG series plot with the ring on the left hand with the external ring electrode contacting the contralateral wrist.
Figure 18:
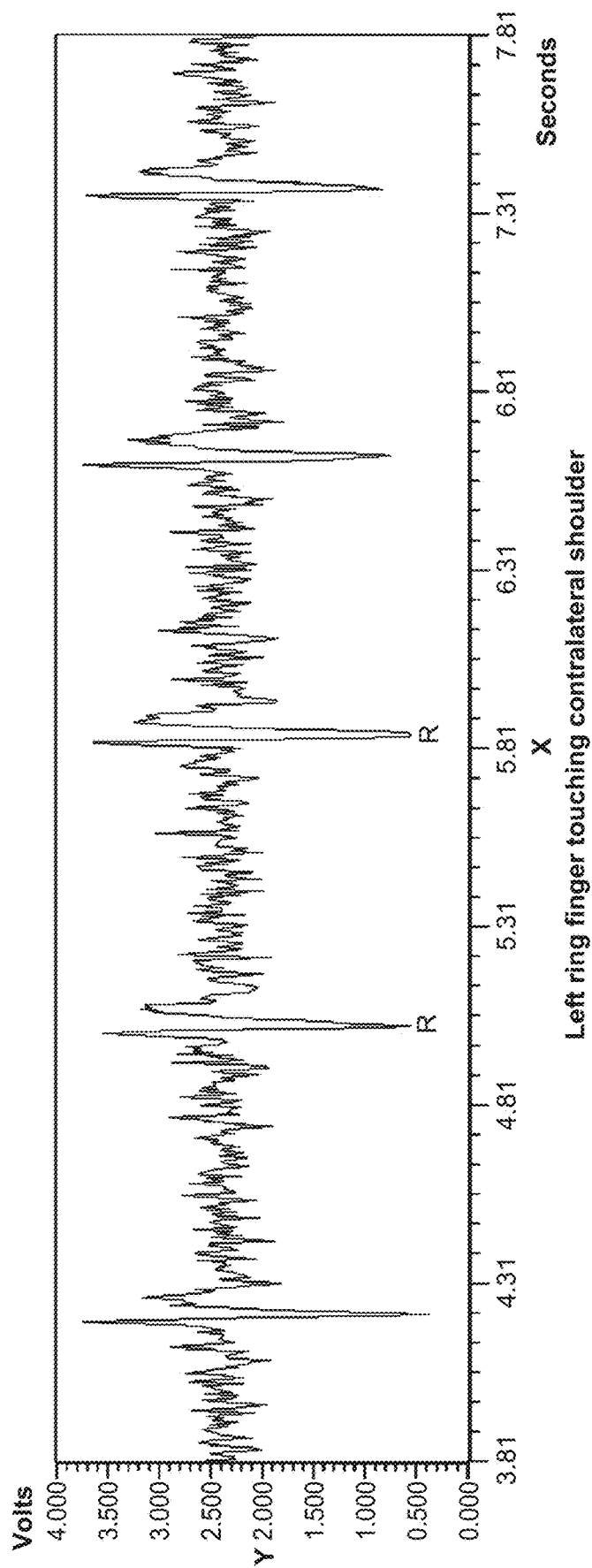
FIG. 18 shows an ECG series plot with the ring on the left hand with the external ring electrode contacting the contralateral shoulder.
Figure 19:
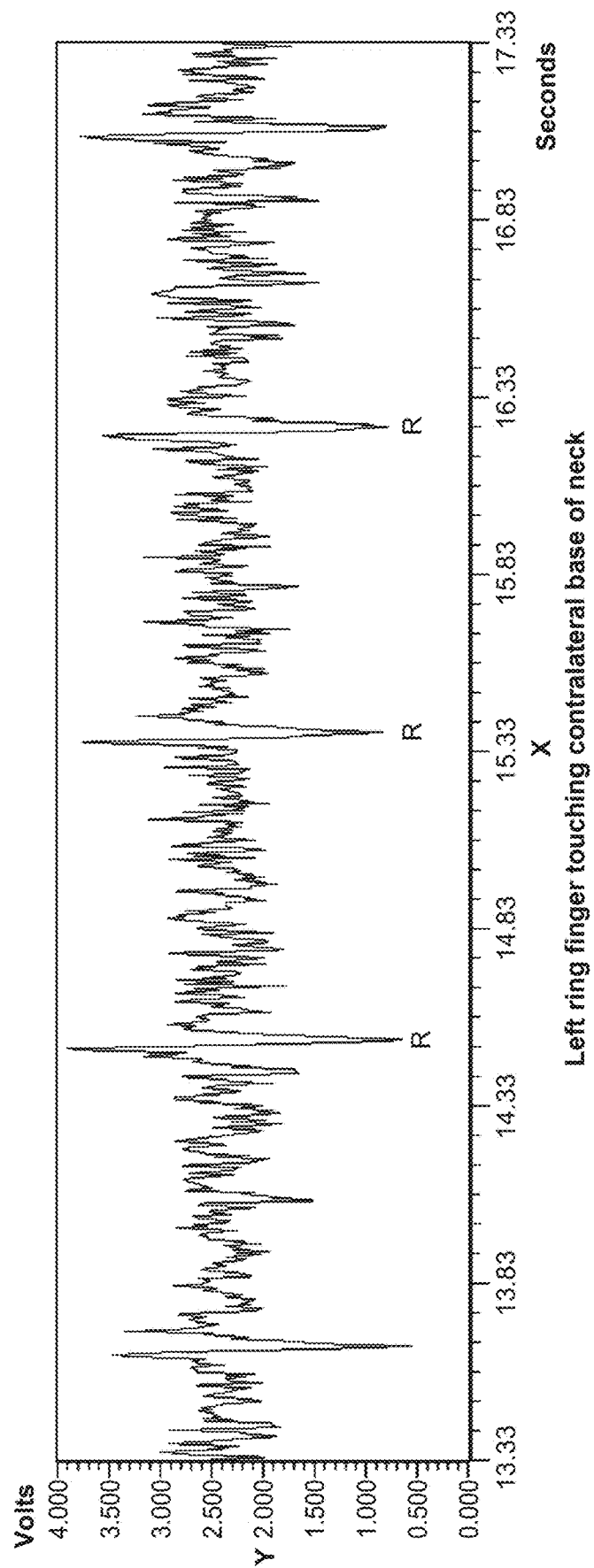
FIG. 19 shows an ECG series plot with the ring on the left hand with the external ring electrode contacting the contralateral base of the neck.
Figure 20:
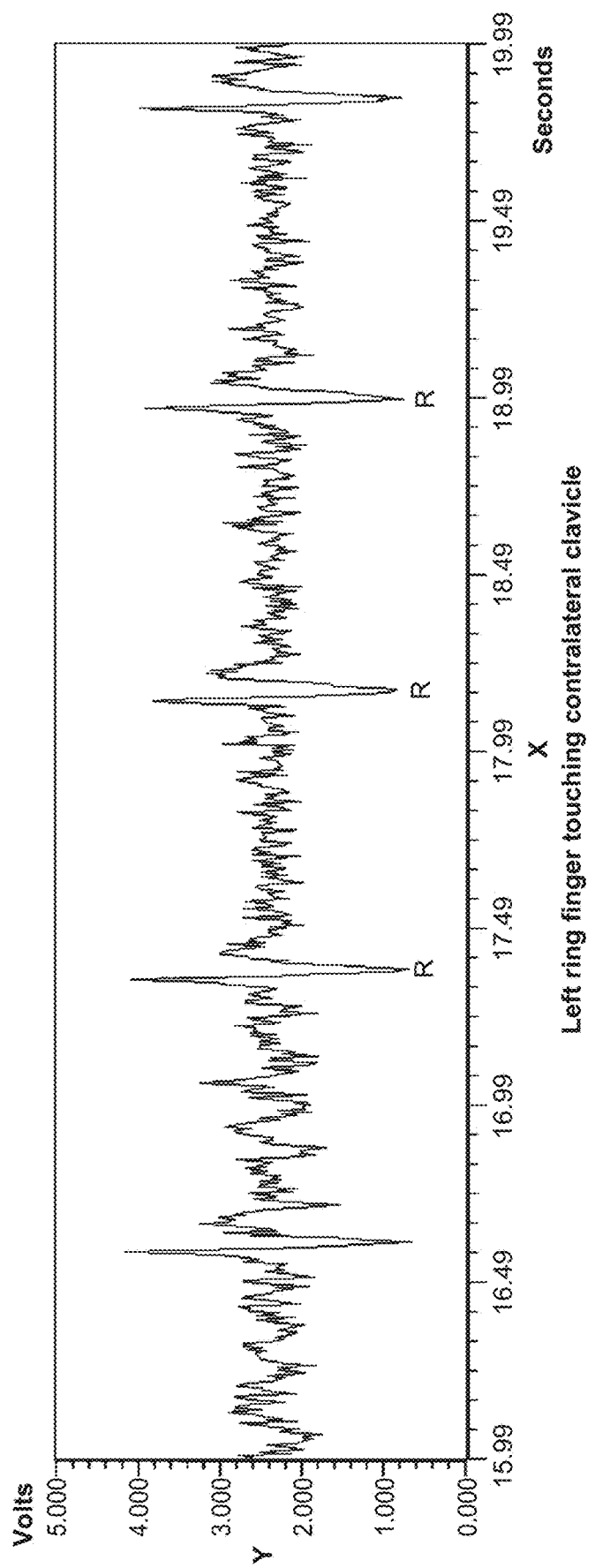
FIG. 20 shows an ECG series plot with the ring on the left hand with the external ring electrode contacting the contralateral clavicle.
Figure 21:
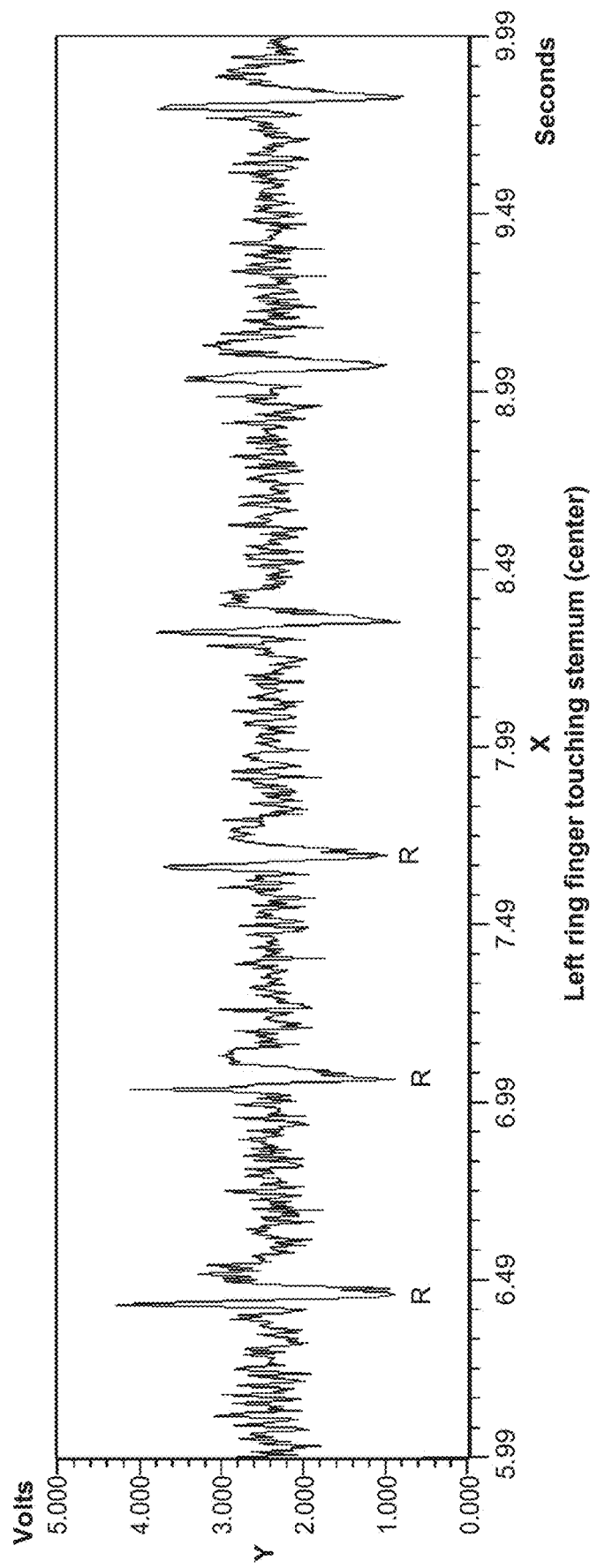
FIG. 21 shows an ECG series plot with the ring on the left hand with the external ring electrode contacting the sternum at the center of the chest.

As shown in FIG. 5, the BP, HR, and HRV calculation algorithms may be implemented within application software 82 to run on a smart phone 78. The numeric outputs of the calculations are displayed on a screen as shown in exemplary screen shot of FIG. 10. In this example, instantaneous HR is displayed in a 60 second scrolling window. Average HR is shown on the left and the number of HR samples is selectable by the user. The HRV value is displayed on the right and the calculation parameters are also user selectable. For instance, the SDRR (standard deviation of the IBIs or RR intervals), an FFT, or a MSSD (square root of the mean of the squared differences between IBIs or RR intervals) calculation can be selected for different HRV use cases. In the center of the FIG. 10 example screen the systolic and diastolic BP are displayed.

In the most current embodiment of the biometric ring, the integrated BLE processor has sufficient internal program memory to perform ECG and PPG peak picking algorithms and HR and HRV calculations on the ring—and then transmit the values to the smart phone for display on the app screen. This capability also enables a variation on the user experience in that a small LCD or LED display on the ring can display the HR and HRV metrics to the user without the need for data streaming to the smart phone.

While incorporating all three of the above-described sensors are preferred, it should be appreciated, however, that the biometric sensor ring of the present disclosure may include fewer or more sensors without departing from the teachings of the present description 4. Experimental Results FIG. 11 through FIG. 16 show a series of ECG recordings with the ring on the left hand touching the ring bottom electrode to the opposite hand and fingers in positions similar to those used in meditation postures: palm, index finger, middle finger, fourth finger, fifth (pinky) finger, and thumb, respectively.

FIG. 17 through FIG. 25 show a series of ECG recordings with the ring 10 on the left hand touching the ring electrode 18c to the following points: contralateral wrist, contralateral shoulder, contralateral neck, contralateral clavicle, sternum, ipsilateral clavicle, ipsilateral shoulder, ipsilateral thigh, and contralateral thigh, respectfully. FIG. 11 through FIG. 25 show good ECG signal to noise ratio (S/N) with the ECG "R" wave component approximately 8 times the amplitude of the average noise level. For instance, the average R wave amplitude is approximately 4 V and the noise floor is generally 0.5 V. A S/N of 3X is sufficient for the peak-picking algorithm (described later) to locate the R wave peaks and thereby calculate the heart rate. As the ring contact point is moved to the ipsilateral side of the body, the R wave amplitude decreases relative to the noise floor. In FIG. 11 through FIG. 25, the ECG data has been amplified by a factor of 4000 with full scale at 4.5 V, and is unfiltered.

Figure 22:
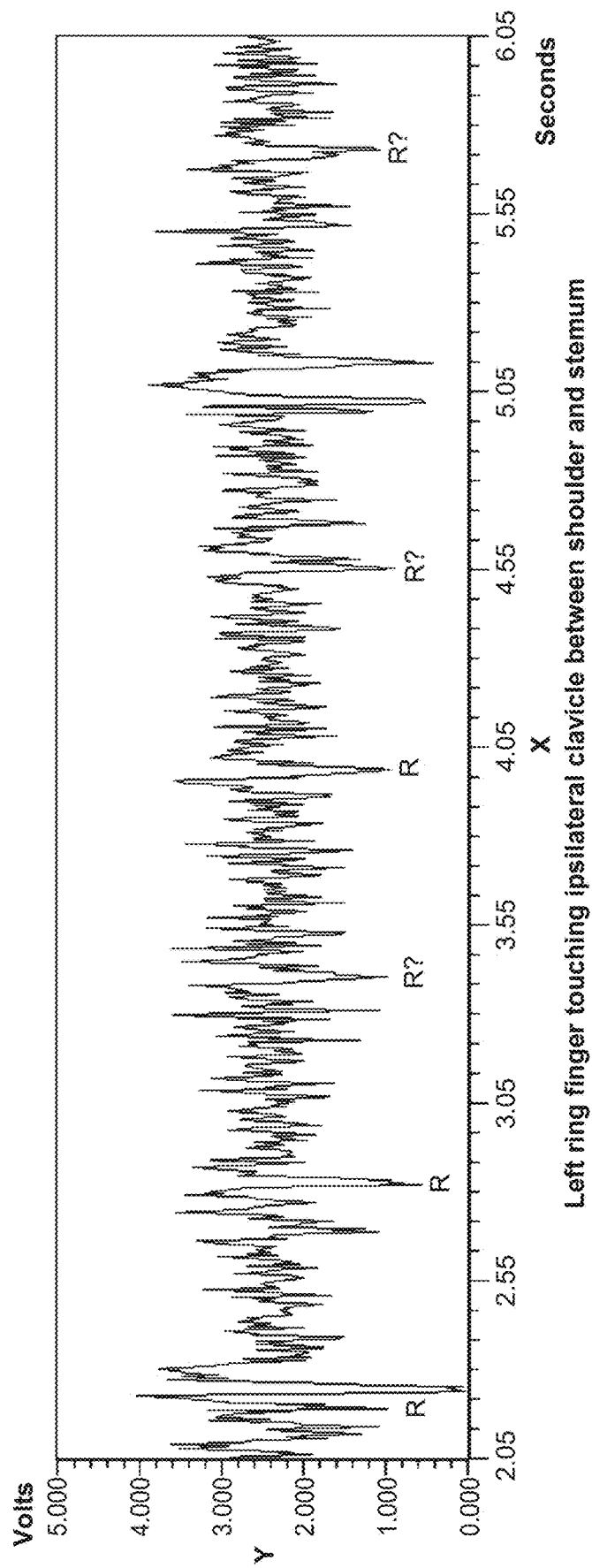
FIG. 22 shows an ECG series plot with the ring on the left hand with the external ring electrode contacting the ipsilateral clavicle half way between the sternum and shoulder.

In FIG. 22, the ring is contacting the clavicle between the sternum and ipsilateral shoulder and the R wave amplitudes are, at most, twice the amplitude of the noise, and often the same as the noise.

Figure 23:
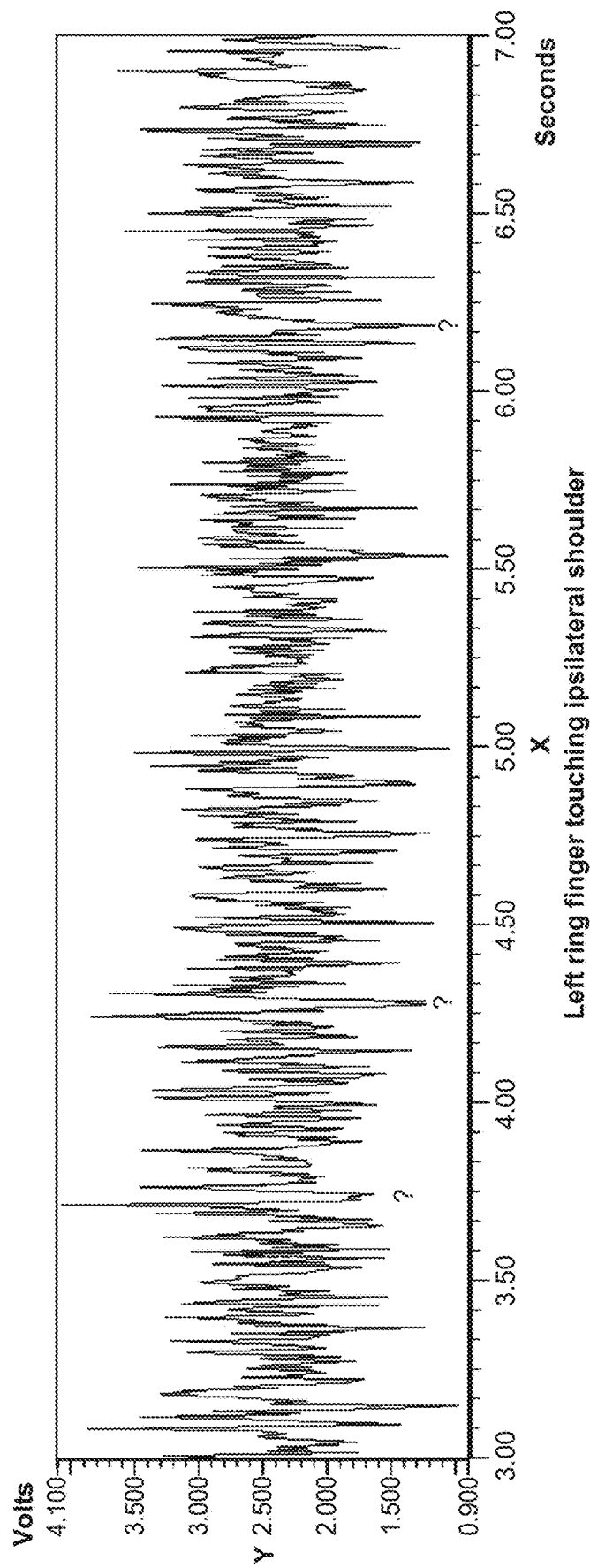
FIG. 23 shows an ECG series plot with the ring on the left hand with the external ring electrode contacting the ipsilateral shoulder.

FIG. 23 shows the ring contacting the ipsilateral shoulder—and the R wave components are completely obscured in the noise. Although it appears that most ipsilateral contact points on the upper torso do not produce a usable R wave, the legs have a different relationship to the ECG wave complex.

Figure 24:
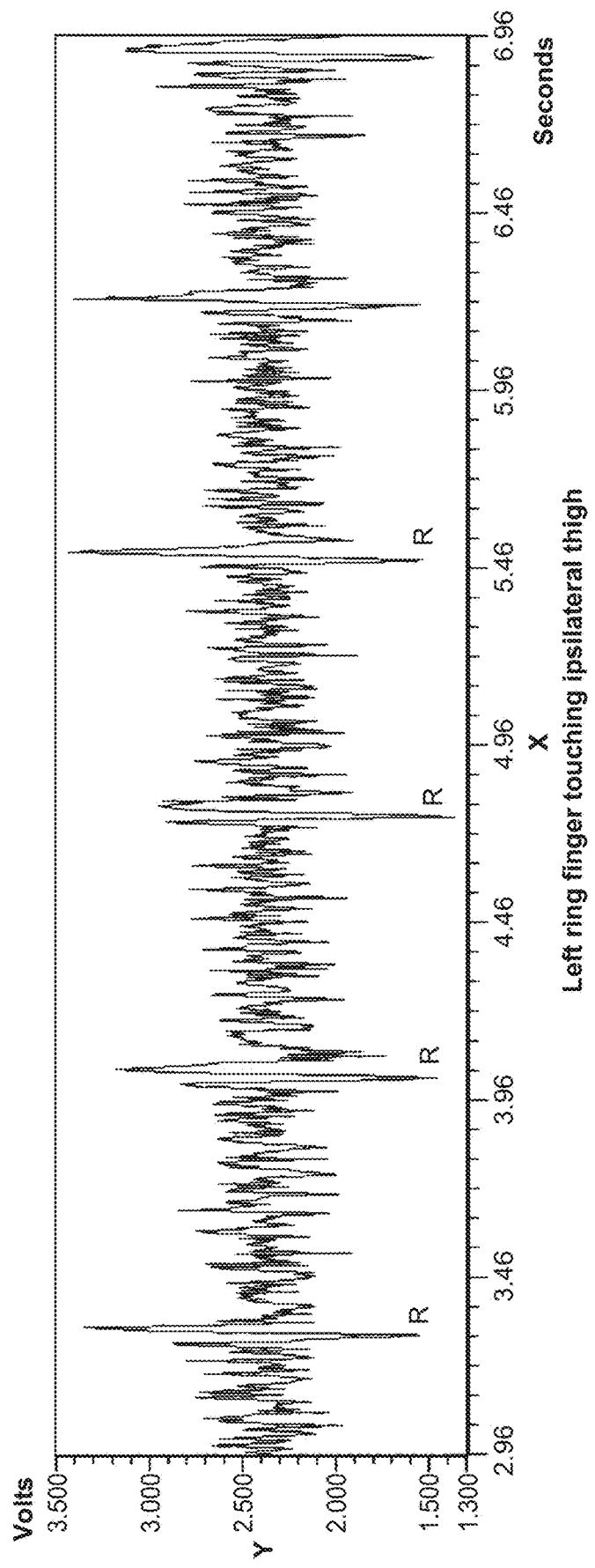
FIG. 24 shows an ECG series plot with the ring on the left hand with the external ring electrode contacting the ipsilateral thigh.

FIG. 24 shows the R wave response with the ring contacting the ipsilateral thigh. The R waves are prominent above an average noise floor of 0.75 V and quite usable for calculating HR. For a runner or other athlete wearing shorts, the ipsilateral hand on the thigh, e.g. left hand on the left thigh, would be the most natural position when sitting, for taking an HR or BP reading.

Figure 25:
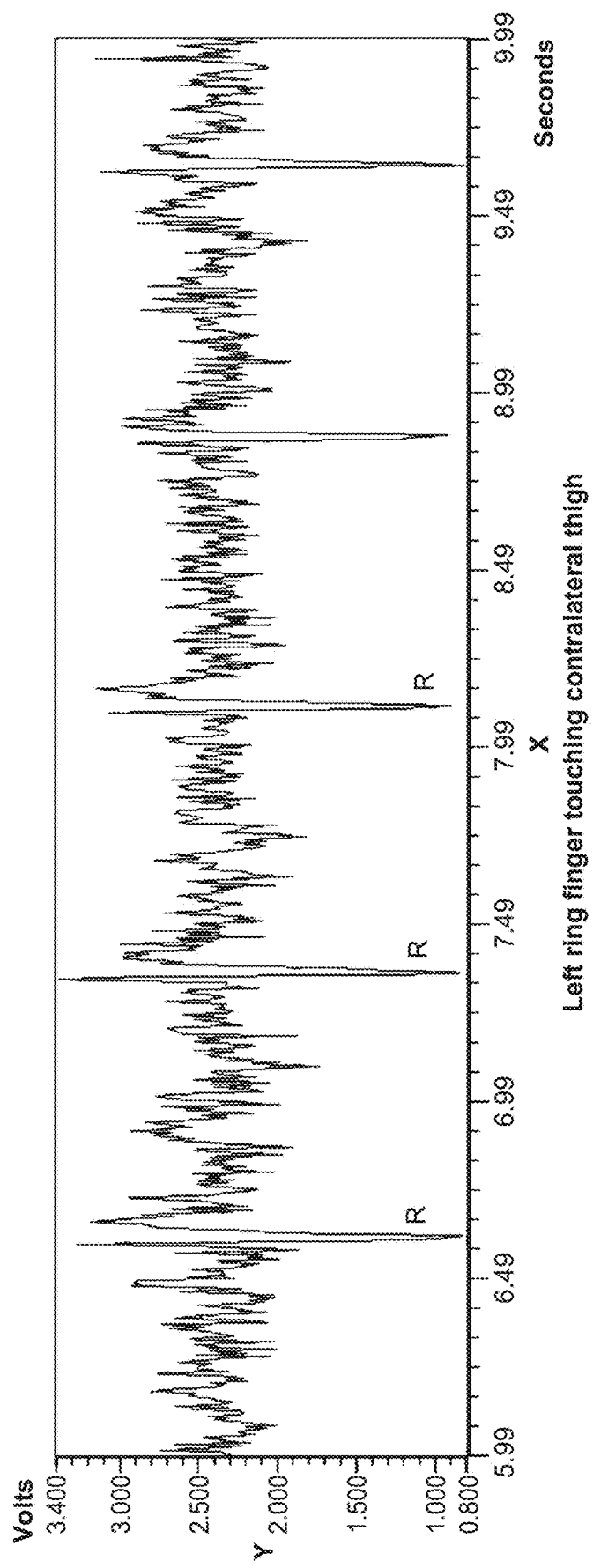
FIG. 25 shows an ECG series plot with the ring on the left hand with the external ring electrode contacting the contralateral thigh.

For comparison, FIG. 25 shows the R response with the ring contacting the contralateral thigh. As we might expect, the S/N is comparable to the other contralateral contact points as shown in FIG. 17 through FIG. 21.

5. General Scope of Embodiments

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general-purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. A wearable biometric sensing apparatus for continuous heart rate and blood pressure monitoring, comprising: (a) a housing having a first surface configured for retention on a skin surface on a first side of a user's body; (b) a photoplethysmograph (PPG) sensor disposed within the housing on the first surface and configured to contact or be placed adjacent the skin surface to register a pulse rate of the user; (c) a first electrode and second electrode disposed within the housing on said first surface and configured to contact the skin; (d) a third electrode disposed on an exterior surface of said housing and configured to allow contact with a contralateral portion of the user's body, wherein said combination of first, second and third electrodes are configured for obtaining electrocardiogram (ECG) measurements; (e) a processor configured to receive data from the PPG sensor and first, second and third electrodes; and (f) a non-transitory memory storing instructions executable by the processor; (g) wherein said instructions, when executed by the processor, perform steps comprising: (i) receiving analog pulse rate data from the PPG sensor and analog ECG data from the first, second and third electrodes; (ii) converting the analog pulse rate data and ECG data into digital data; (iii) calculating one or more of heart rate (HR), heart rate variability (HRV) and blood pressure (BP) from a combination of the digital ECG and PPG sensor data; and (iv) outputting one or more of the calculated HR, HRV and BP.

2. The apparatus or method of any preceding or subsequent embodiment, wherein BP is calculated by determining a time difference between an ECG wave peak and a PPG wave peak extracted from the digital ECG and PPG sensor data.

3. The apparatus or method of any preceding or subsequent embodiment, wherein said instructions when executed by the processor further perform steps comprising: (v) deriving user cardiac electrical activity from said ECG data as temporally compared to PPG heart rate information.

4. The apparatus or method of any preceding or subsequent embodiment, further comprising: (h) a communication circuit configured for wirelessly communicating between said wearable biometric sensing apparatus and a mobile device; (i) wherein said instructions when executed by the processor further perform steps comprising: (vi) communicating data relating to HR, HRV, and BP over said communication circuit to the mobile device; and (vii) graphically displaying HR, HRV, and BP on the mobile device.

5. The apparatus or method of any preceding or subsequent embodiment: wherein the housing comprises a ring housing that is configured for retention on a finger of the user; wherein said first and second electrodes are disposed on the bottom interior of an aperture the ring housing to contact skin on a palmer side of the user's finger; and wherein said third electrode is on an outer surface of the ring housing to contact a portion of the user separate from the hand upon which the housing is retained upon.

6. The apparatus or method of any preceding or subsequent embodiment, wherein the portion comprises one of: a finger from an opposite hand; contralateral wrist; contralateral shoulder; contralateral neck; contralateral clavicle, sternum, ipsilateral clavicle, ipsilateral shoulder, ipsilateral thigh, and contralateral thigh of the user.

7. The apparatus or method of any preceding or subsequent embodiment, wherein the first and second electrodes further form an electrodermal activity (EDA) sensor configured for measuring changes in skin impedance indicative of sympathetic nervous system (SNS) activation.

8. The apparatus or method of any preceding or subsequent embodiment, wherein said instructions when executed by the processor further perform steps comprising: (viii) evaluating a combination of digital ECG, EDA and PPG sensor data to determine a physiological state assessment of the user.

9. The apparatus or method of any preceding or subsequent embodiment, further comprising: (j) an energy storage unit integrated within or attached to said ring housing for supplying electrical power to said PPG sensor, first electrode second electrode, third electrode, said communication circuit.

10. The apparatus or method of any preceding or subsequent embodiment, wherein controlling operation of said apparatus, collecting sensor data from said apparatus, analyzing collected sensor data from the apparatus to generate analyzed data, and displaying collected sensor data or analyzed data is performed from the mobile device.

11. A method for continuous heart rate and blood pressure monitoring, comprising: (a) positioning a wearable biometric sensing apparatus on a skin surface on a first side of a user's body; (b) directing a photoplethysmograph (PPG) sensor disposed within the sensing apparatus toward the skin surface to register a pulse rate of the user; (c) contacting a first electrode and second electrode disposed within the sensing skin surface; (d) contacting a third electrode on an exterior surface of the sensing apparatus on a contralateral portion of the user's body, wherein said combination of first, second and third electrodes are configured for obtaining electrocardiogram (ECG) measurements; (e) receiving analog pulse rate data from the PPG sensor and analog ECG data from the first, second and third electrodes; (f) converting the analog pulse rate data and ECG data into digital data; (g) calculating one or more of heart rate (HR), heart rate variability (HRV) and blood pressure (BP) from a combination of the digital ECG and PPG sensor data; and (h) graphically outputting one or more of the calculated HR, HRV and BP.

12. The apparatus or method of any preceding or subsequent embodiment, wherein BP is calculated by determining a time difference between an ECG wave peak and a PPG wave peak extracted from the digital ECG and PPG sensor data.

13. The apparatus or method of any preceding or subsequent embodiment, further comprising: (i) deriving user cardiac electrical activity from said ECG data as temporally compared to heart rate information.

14. The apparatus or method of any preceding or subsequent embodiment, further comprising: (j) wirelessly communicating data relating to HR, HRV, and BP between said sensing ring and a mobile device; and (k) graphically displaying HR, HRV, and BP on the mobile device.

15. The apparatus or method of any preceding or subsequent embodiment: wherein the housing is a ring housing retained on a finger of the user; wherein said first and second electrodes are disposed on the bottom interior of an aperture the ring housing to contact skin on a palmer side of the user's finger; and wherein said third electrode is on an outer surface of the ring housing to contact a portion of the user separate from the hand upon which the housing is retained upon.

16. The apparatus or method of any preceding or subsequent embodiment, wherein the portion comprises one of: a finger from an opposite hand; contralateral wrist; contralateral shoulder; contralateral neck; contralateral clavicle, sternum, ipsilateral clavicle, ipsilateral shoulder, ipsilateral thigh, and contralateral thigh of the user.

17. The apparatus or method of any preceding or subsequent embodiment, wherein the first and second electrodes further form an electrodermal activity (EDA) sensor configured for measuring changes in skin impedance indicative of sympathetic nervous system (SNS) activation.

18. The apparatus or method of any preceding or subsequent embodiment, further comprising: evaluating a combination of digital ECG, EDA and PPG sensor data to determine a physiological state assessment of the user.

19. The apparatus or method of any preceding or subsequent embodiment, further comprising: supplying electrical power to said PPG sensor, first electrode second electrode, third electrode, said communication circuit via an electrical storage contained within the sensor ring.

20. The apparatus or method of any preceding or subsequent embodiment: wherein controlling operation of said apparatus, collecting sensor data from said apparatus, analyzing collected sensor data from the apparatus to generate analyzed data, and displaying collected sensor data or analyzed data is performed from the mobile device.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A wearable biometric sensing ring apparatus for continuous heart rate and blood pressure monitoring, comprising:
    (a) a ring-shaped housing having a finger aperture with a flexible circuit board having a first surface configured for retention on a skin surface on any finger of a user's hand on a first side of a user's body;
    (b) a photoplethysmograph (PPG) sensor disposed on said first surface of said flexible circuit board and configured to contact or be placed adjacent the skin surface to register a pulse rate of the user;
    (c) a rigid sensor surface attached along said first surface of said flexible circuit board upon which are mounted a first electrode and second electrode which are configured to contact the skin of a finger of the user while minimizing motion artifacts;
    (d) a third electrode disposed on an exterior surface of said housing and having a free sensing surface configured for establishing direct contact with a contralateral portion of the user's body, as a second side of the user's body, wherein said combination of first, second and third electrodes are configured for obtaining electrocardiogram (ECG) measurements;
    (e) a processor disposed on said flexible circuit board, said processor configured to receive data from the PPG sensor and first, second and third electrodes; and
    (f) a non-transitory memory storing instructions executable by the processor;
    (g) wherein said instructions, when executed by the processor, perform steps comprising:
        (i) receiving analog pulse rate data from the PPG sensor and analog ECG data from the first, second and third electrodes;
        (ii) converting the analog pulse rate data and ECG data into digital data;
        (iii) calculating blood pressure (BP) from a combination of the digital ECG and PPG sensor data, wherein BP is calculated by determining a time difference between an ECG wave peak and a PPG wave peak extracted from the digital ECG and PPG sensor data to generate a pulse transit time (PTT), and calibrating a set of PTT measurements against standard BP measurements to determine a user's variance from a standard measure as a function of one or more of the user's due height and weight; and
        (iv) outputting BP;
    (h) wherein said first and second electrodes are disposed on said first surface which is a bottom interior surface of the aperture of the ring housing to contact skin on a palmar side of the user's finger upon which the ring-shaped housing is retained; and
    (i) wherein said third electrode is located on an outer surface of the ring housing at a location to allow for contact with a portion of the user separate from the hand upon which the housing is retained.

2. The apparatus of claim 1, further comprising calculating one or more of heart rate (HR) and heart rate variability (HRV) in addition to BP, and outputting one or more of the HR and HRV along with the BP.

3. The apparatus of claim 2, further comprising:
    (k) a communication circuit configured for wirelessly communicating between said wearable biometric sensing apparatus and a mobile device;
    (l) wherein said instructions when executed by the processor further perform steps comprising:
        (v) communicating data relating to HR, HRV, and BP over said communication circuit to the mobile device for graphic display of HR, HRV, and BP on the mobile device.

4. The apparatus as recited in claim 3, wherein the instructions and communication circuit are configured to allow for controlling operation of said apparatus, collecting sensor data from said apparatus, analyzing collected sensor data from the apparatus, and displaying the collected sensor data from the mobile device.

5. The apparatus of claim 1, wherein said instructions when executed by the processor further perform steps comprising:
    (v) deriving user cardiac electrical activity from said ECG data as temporally compared to PPG heart rate information.

6. The apparatus as recited in claim 1:
    wherein said third electrode is disposed on an outer dorsally-located surface of the ring housing to contact a portion of the user separate from the hand upon which the housing is retained upon.

7. The apparatus as recited in claim 1, wherein said third electrode is located at a location on the outer surface of the ring housing to allow for contact with: a finger from an opposite hand; contralateral wrist; contralateral shoulder;
    contralateral neck; contralateral clavicle, sternum, ipsilateral clavicle, ipsilateral shoulder, ipsilateral thigh, and contralateral thigh of the user.

8. The apparatus as recited in claim 1, wherein the first and second electrodes further form an electrodermal activity (EDA) sensor configured for measuring changes in skin impedance indicative of sympathetic nervous system (SNS) activation.

9. The apparatus as recited in claim 8, wherein said instructions when executed by the processor further perform steps comprising:
(vi) evaluating a combination of digital ECG, EDA and PPG sensor data to determine a physiological state assessment of the user.

10. The apparatus as recited in claim 1, further comprising:
(k) an energy storage unit integrated within or attached to said ring housing for supplying electrical power to said PPG sensor, first electrode second electrode, third electrode, said communication circuit.

11. A method for continuous heart rate and blood pressure monitoring on a finger ring, comprising:
(a) positioning a finger ring wearable biometric sensing apparatus comprising a ring-shaped housing on a finger of a user's body, the housing having an aperture that is configured for retention on the finger and first and second electrodes disposed on a rigid sensor surface attached on a flexible circuit at the bottom interior surface of the aperture of the ring-shaped housing to contact skin on a palmar side of the user's finger upon which the ring-shaped housing is retained;
(b) directing a photoplethysmograph (PPG) sensor disposed on or at least partially within the housing of the sensing apparatus toward a skin surface on the finger to register a pulse rate of the user;
(c) contacting the first electrode and second electrode with a skin surface on the palmar side of the user's finger;
(d) moving said finger ring wearable biometric sensing apparatus for contacting a third electrode located on an exterior surface opposite the bottom interior surface of the ring-shaped housing with a contralateral portion of the user's body, wherein said combination of first, second and third electrodes are configured for obtaining electrocardiogram (ECG) measurements;
(e) receiving analog pulse rate data from the PPG sensor and analog ECG data from the first, second and third electrodes;
(f) converting the analog pulse rate data and ECG data into digital data;
(g) calculating blood pressure (BP) from a combination of the digital ECG and PPG sensor data, wherein BP is calculated by determining a time difference between an ECG wave peak and a PPG wave peak extracted from the digital ECG and PPG sensor data to generate a the pulse transit time (PTT), and calibrating a set of PTT measurements against standard BP measurements to determine a user's variance from a standard measure as a function of one or more of the user's due height and weight; and
(h) graphically outputting the calculated BP.

12. The method of claim 11, further comprising calculating one or more of heart rate (HR) and heart rate variability (HRV) in addition to BP, and outputting one or more of the HR and HRV along with the BP.

13. The method of claim 11, further comprising:
(i) deriving user cardiac electrical activity from said ECG data as temporally compared to heart rate information.

14. The method of claim 13, further comprising:
(j) wirelessly communicating data relating to HR, HRV, and BP between said sensing ring and a mobile device for graphic display of HR, HRV, and BP on the mobile device.

15. The method as recited in claim 14, further comprising:
controlling operation of said apparatus, collecting sensor data from said apparatus, analyzing collected sensor data from the apparatus, and displaying collected sensor data from the mobile device.

16. The method as recited in claim 11:
wherein said third electrode is disposed on an outer dorsally-located surface of the ring housing to contact a portion of the user separate from the hand upon which the housing is retained upon.

17. The method as recited in claim 11, wherein said third electrode is located at a location on the outer surface of the ring housing to allow for contact with a finger from an opposite hand; contralateral wrist; contralateral shoulder; contralateral neck; contralateral clavicle, sternum, ipsilateral clavicle, ipsilateral shoulder, ipsilateral thigh, and contralateral thigh of the user.

18. The method as recited in claim 11, wherein the first and second electrodes further form an electrodermal activity (EDA) sensor configured for measuring changes in skin impedance indicative of sympathetic nervous system (SNS) activation.

19. The method as recited in claim 18, further comprising:
evaluating a combination of digital ECG, EDA and PPG sensor data to determine a physiological state assessment of the user.

20. The method as recited in claim 11, further comprising:
supplying electrical power to said PPG sensor, first electrode second electrode, third electrode, said communication circuit via an electrical storage contained within the sensor ring.

* * * * *